United States Patent
Kelso et al.

(10) Patent No.: US 11,028,358 B2
(45) Date of Patent: Jun. 8, 2021

(54) CELL CULTURE LASER PHOTOABLATION

(71) Applicant: Synthego Corporation, Redwood City, CA (US)

(72) Inventors: Reed Kelso, San Francisco, CA (US); Travis Maures, Pacifica, CA (US)

(73) Assignee: Synthego Corporation, Menlo Park, CA (US)

( * ) Notice: Subject to any disclaimer, the term of this patent is extended or adjusted under 35 U.S.C. 154(b) by 0 days.

(21) Appl. No.: 16/803,218

(22) Filed: Feb. 27, 2020

(65) Prior Publication Data

US 2020/0270560 A1    Aug. 27, 2020

Related U.S. Application Data

(60) Provisional application No. 62/811,340, filed on Feb. 27, 2019.

(51) Int. Cl.
*C12M 1/00* (2006.01)
*C12M 1/36* (2006.01)
*C12Q 1/02* (2006.01)

(52) U.S. Cl.
CPC ............ *C12M 31/00* (2013.01); *C12M 41/06* (2013.01); *C12M 41/48* (2013.01); *C12Q 1/02* (2013.01)

(58) Field of Classification Search
None
See application file for complete search history.

(56) References Cited

U.S. PATENT DOCUMENTS

| | | | |
|---|---|---|---|
| 6,773,903 | B2 | 8/2004 | Bova |
| 8,753,855 | B2 | 6/2014 | Nakashima et al. |
| 2018/0142193 | A1 | 5/2018 | Suzuki et al. |
| 2018/0354076 | A1 | 12/2018 | Suzuki et al. |

FOREIGN PATENT DOCUMENTS

| | | |
|---|---|---|
| EP | 3305888 A1 | 4/2018 |
| EP | 3315600 A1 | 5/2018 |
| EP | 3467091 A1 | 4/2019 |
| WO | WO-2006088154 A1 | 8/2006 |
| WO | WO-2010081171 A2 | 7/2010 |
| WO | WO-2016194454 A1 | 12/2016 |
| WO | WO-2017208589 A1 | 12/2017 |
| WO | WO-2018146854 A1 | 8/2018 |
| WO | WO-2019046304 A1 | 3/2019 |
| WO | WO-2020033871 A1 | 2/2020 |
| WO | WO-2020097083 A1 | 5/2020 |
| WO | WO-2020176798 A1 | 9/2020 |

OTHER PUBLICATIONS

Hanania et al. Automated in Situ Measurement of Cell-Specific Antibody Secretion and Laser-Mediated Purification for Rapid Cloning of Highly-Secreting Producers. Biotechnol Bioeng. Sep. 30, 2005;91(7):872-6.doi: 10.1002/bit.20559.

PCT/US2020/020225 International Search Report and Written Opinion dated Jun. 9, 2020.

Stich et al. Live Cell Catapulting and Recultivation. Pathol Res Pract. 2003;199(6):405-9.doi: 10.1078/0344-0338-00437.

Szaniszlo et al. Scanning Cytometry With a LEAP: Laser-Enabled Analysis and Processing of Live Cells in Situ.Cytometry A. Jul. 2006;69(7):641-51.doi: 10.1002/cyto.a.20291.

Teramura et al. Laser-assisted Cell Removing (LACR) Technology Contributes to the Purification Process of the Undifferentiated Cell Fraction During Pluripotent Stem Cell Culture. Biochem Biophys Res. Sep. 18, 2018;503(4):3114-3120.doi: 10.1016/j.bbrc.2018.08.101. Epub Aug. 22, 2018.

Zordan et al. Photoablative dilution with pre-enrichment for the clonal isolation of rare cancer cells. Proc. of SPIE vol. 7182 71820Z-1 (2009). 7 pages.

Baac et al. Micro-ultrasonic cleaving of cell clusters by laser-generated focused ultrasound and its mechanisms. Biomed Opt Express 4(8):1442-1450 (2013).

Boyce et al. Novel millimeter-wave-based method for in situ cell isolation and other applications. Sci Rep 2018; 8:14755. Published online Oct. 3, 2018. doi: 10.1038/s41598-018-32950-w. 17 pages.

Carey et al. Developments in label-free microfluidic methods for single-cell analysis and sorting. WIREs 11(1):e1529 (Jan./Feb. 2019). First published Apr. 24, 2018.

Chen et al. Selective single cell detachment and retrieval for downstream analyses using nanosecond laser pulses in cnt-coated microwell arrays. 19th International Conference on Miniaturized Systems for Chemistry and Life Sciences, pp. 224-226, Oct. 25-29, 2015, Gyeongju, Korea.

Ettensohn. Cell interactions in the sea urchin embryo studied by fluorescence photoablation. Science. Jun. 1, 1990;248(4959):1115-8.

Fan et al. Localized Single-Cell Lysis and Manipulation Using Optothermally-Induced Bubbles. Micromachines (Basel). Apr. 2017; 8(4): 121.Published online Apr. 11, 2017. doi: 10.3390/mi8040121. 13 pages.

Gu et al. Detachment and reorientation of cells using near-infrared laser microbeam. Journal of Biomedical Optics 16(11):115002 (Nov. 2011). Published online Oct. 31, 2011. 6 pages.

Hayashi et al. Automated adherent cell elimination by a high-speed laser mediated by a light-responsive polymer. Commun Biol. 2018; 1:218. Published online Dec. 7, 2018.doi: 10.1038/s42003-018-0222-4. 9 pages.

Hosokawa et al. Noncontact estimation of intercellular breaking force using a femtosecond laser impulse quantified by atomic force microscopy. Proc Natl Acad Sci U S A. Feb. 1, 2011; 108(5):1777-1782. Published online Jan. 18, 2011. doi: 10.1073/pnas. 1006847108.

(Continued)

*Primary Examiner* — Robert J Yamasaki
(74) *Attorney, Agent, or Firm* — Wilson Sonsini Goodrich & Rosati

(57) ABSTRACT

Methods and systems for preparing clonal cell populations are described. In some instances the disclosed methods comprise: a) identifying and selecting a cell based on its position on a surface or in a container, where the selection is not based on whether the cell comprises an exogenous label or an expressed reporter; b) photoablating all non-selected cells on the surface or in the container; and c) growing a clonal population of the selected cell.

20 Claims, 10 Drawing Sheets

(56) References Cited

OTHER PUBLICATIONS

Kahlili et al. A Review of Cell Adhesion Studies for Biomedical and Biological Applications. Int J Mol Sci. Aug. 2015; 16(8):18149-18184. Published online Aug. 5, 2015. doi: 10.3390/ijms160818149.

Kataoka Product Information—Life Sciences. Retrieved Mar. 16, 2020 from URL: <http://www.kataoka-ss.co.jp/english/item/life_science.php>. 5 pages.

Kimble. Alterations in cell lineage following laser ablation of cells in the somatic gonad of Caenorhabditis elegans. Developmental Biology 87(2): 286-300 (1981).

Koller et al. High-throughput laser-mediated in situ cell purification with high purity and yield. Cytometry Part A 61A:153-161 (2004). Published online Aug. 27, 2004.

Lim et al. Differential detachment of intact and viable cells of different sizes using laser-induced microbubbles. Biomed Opt Express. Oct. 1, 2019; 10(10):4919-4930. Published online Sep. 4, 2019. doi: 10.1364/BOE.10.004919.. 0.

Ma et al., Multicolor CRISPR labeling of chromosomal loci in human cells, Proc Natl Acad Sci U S A., 112(10): 3002-3007 (2015).

Makhijani et al. Precision Optogenetic Tool for Selective Single-and Multiple-Cell Ablation in a Live Animal Model System. Cell Chem Biol. Jan. 19, 2017; 24(1):110-119. Published online Jan. 5, 2017. doi: 10.1016/j.chembiol.2016.12.010.

Ojima et al. Different methods of detaching adherent cells significantly affect the detection of stem cell antigens in synovial mesenchymal stem cells. Abstracts/Osteoarthritis and Cartilage 24:S509-S510 (2016).

Shen et al. Toward complete laser ablation of melanoma contaminant cells in a co-culture outgrowth model via image cytometry. Cytometry A. Jul. 2006;69(7):573-81. Published online Jun. 19, 2006.

Siddiqi et al. Specific collection of adherent cells using laser release in a droplet-driven capillary cell. J Biomed Opt Nov.-Dec. 2010;15(6):065003. Epub Nov. 24, 2010. doi: 10.1117/1.3523365. 6 pages.

Simon et al. Adherent Cell Culture in Biopharmaceutical Applications: The Cell-Detachment Challenge. Process Development Forum (Mar. 16, 2016). Retrieved Sep. 16, 2019 from URL: <http://www.processdevelopmentforum.com/articles/adherent-cell-culture-in-biopharmaceutical-applications-the-cell-detachment-challenge/>. 7 pages.

Soustelle et al. UV laser mediated cell selective destruction by confocal microscopy. Neural Develop. 2008; 3:11. Published online Apr. 28, 2008. doi: 10.1186/1749-8104-3-11. 8 pages.

Stiletto Infrared Laser System for Research: Adherent Cell Culture Research Applications (Brochure). Hamilton Thorne (Nov. 1, 2018). Retrieved Mar. 16, 2020 from URL: <https://www.hamiltonthorne.com/index.php/research-lasers/research-laser-brochures/book/21-stiletto-2018/4-research-laser-brochures?tmpl=component>. 4 pages.

Sumaru et al. On-Plate and On-Demand Removal of Adherent Cells using Photo-Acid-Generating Substrate and Micro-Projection System. 16th International Conference on Miniaturized Systems for Chemistry and Life Sciences, Okinawa, Japan, pp. 100-102, Oct. 28-Nov. 1, 2012.

Terstegge et al. Laser-Assisted Photoablation of Human Pluripotent Stem Cells from Differentiating Cultures. Stem Cell Reviews and Reports 6:260-269 (2010). Published online Feb. 26, 2010.

Várady et al. Cell surface membrane proteins as personalized biomarkers: where we stand and where we are headed. Biomark Med. Oct. 2013;7(5):803-19. doi: 10.2217/bmm.13.90.

Xiao et al. Optically micropatterned culture of adherent cells. J Biomed Opt. Jul. 2012;17(7):075004. Epub Jul. 9, 2012. doi: 10.1117/1.JBO.17.7.075004.

XYClone and XYRCOS Research Laser Systems (Brochure). Hamilton Thorne (Dec. 3, 2018). Retrieved Mar. 16, 2020 from URL: <https://www.hamiltonthorne.com/index.php/research-lasers/research-laser-brochures/book/23-2018-xyclone-xyrcos-brochure/4-research-laser-brochures?tmpl=component>. 6 pages.

Zeigler et al. Laser Selection Significantly Affects Cell Viability Following Single-Cell Nanosurgery. Photochemistry and Photobiology 85(5):1218-1224 (Sep./Oct. 2009).

Zhang et al. Sacrificial-layer free transfer of mammalian cells using near infrared femtosecond laser pulses. PLoS ONE 13(5):e0195479 (May 2, 2018). 11 pages.

Zheng et al. Cell detachment: post-isolation challenges. Biotechnol Adv. Dec. 2013;31(8):1664-75. doi: 10.1016/j.biotechadv.2013.08.013. Epub Aug. 24, 2013.

CELL CULTURE LASER PHOTOABLATION

CROSS-REFERENCE

This application claims the benefit of U.S. Provisional Application No. 62/811,340, filed on Feb. 27, 2019, which application is incorporated herein by reference.

BACKGROUND

Methods and systems for creating homogeneous clonal cell populations have become increasingly important for a variety of emerging applications including, but not limited to, expression and purification of genetically-engineered proteins, nucleic acids, and other cellular components; production of biologic drugs (biologics); and therapeutic applications of stem cells. One approach to creating homogeneous clonal populations of cells is to grow cell populations in culture, and then selectively remove or destroy "contaminant" cells (e.g., using micropipettes or other physical probes, optical "tweezers", or laser photoablation). This approach can become increasingly cumbersome and inefficient as the number of contaminant cells, or percentage of contaminant cells in the cell culture, to be removed or destroyed becomes larger. A far more efficient approach can be to isolate a single cell prior to culturing in a contamination-free environment, thereby ensuring that the resulting cell culture is a homogeneous clonal cell population.

Existing methods for generating clones from single cells can focus primarily on the use of serial dilution techniques and/or microfluidic devices to deposit a single cell in a culture plate well or other container and subsequently incubating it under appropriate conditions to ensure that it divides and develops into a mature clonal population. A challenge with the former is that random deposition of a cell suspension that is dilute enough to ensure that, on average, each culture plate well contains only a single cell can also ensure that many of the culture plate wells will be empty (as is well known and predicted by the Poisson distribution). This can lead to a very inefficient process in terms of the number of culture plate wells that must be processed and can also require subsequent characterization of the population in each well to ensure that it does indeed contain a cell culture that arose from a single cell. Alternatively, microfluidic device-based approaches are often prone to clogging and can subject the cells to mechanical stress that can negatively impact their viability. Thus, there is an unmet need for new methods and technologies that provide a means for fast, efficient processing of cells and culture plates to produce clonal cell populations at a commercial scale.

SUMMARY

Disclosed herein are methods comprising, for each of one or more partitioned surfaces or containers, a) selecting a cell based on its position on the partitioned surface or in the container, thereby identifying a selected cell, wherein the selecting is not based on whether the cell comprises an exogenous label or an expressed reporter; and b) photoablating non-selected cells on the partitioned surface or in the container, wherein at least 90% of the one or more partitioned surfaces or containers comprise only the selected cell as a viable cell after the photoablating is performed. In some embodiments, at least 95% of the one or more partitioned surfaces or containers comprise only the selected cell as the viable cell after the photoablating is performed. In some embodiments, the one or more partitioned surfaces or containers comprise at least 5, 10, 20, 30, 40, 50, 60, 70, 80, 90, or 100 partitioned surfaces or containers.

Also disclosed herein are methods comprising: photoablating all but a first cell of two or more cells on a surface or in a container. In some embodiments, the method further comprises growing a clonal population of the first cell after the photoabalating is performed. In some embodiments, the first cell is selected using an imaging technique. In some embodiments, the method further comprises selecting the first cell using an automated image analysis process. In some embodiments, the selecting is based on a proximity of the first cell to a center of the surface or the container, a size of the first cell, a morphology of the first cell, a phenotype of the first cell, a development stage of the first cell, one or more biomarkers, or any combination thereof. In some embodiments, the selecting is based on one or more biomarkers, and the one or more biomarkers comprise a genetically-engineered protein. In some embodiments, the selecting is based on the one or more biomarkers, and the one or more biomarkers comprise one or more cell surface receptors or one or more fluorescent signals that are derived from fluorescent probes of cellular metabolic state. In some embodiments, the selecting is based on detection of a CRISPR editing success parameter. In some embodiments, the CRISPR editing success parameter comprises a Cas-dependent fluorescent moiety. In some embodiments, the Cas9-dependent fluorescent moiety is a Cas-GFP construct. In some embodiments, the two or more cells comprise about 10 to about 15 cells. In some embodiments, cells are photoablated at a rate of at least 60 cells per minute. In some embodiments, cells are photoablated with an efficiency of greater than 99%. In some embodiments, cells are photoablated using light in the wavelength range of 1440 nm to 1450 nm.

Disclosed herein are methods comprising photoablating at least 80% of five or more cells in each of a plurality of culture plate wells, wherein at least 95% of the plurality of culture plate wells contain only one viable cell after the photoablating is performed. In some embodiments, at least 98% of the plurality of culture plate wells contain only one viable cell after the photoablating is performed. In some embodiments, the plurality of culture plate wells comprises at least 5, 10, 20, 30, 40, 50, 60, 70, 80, 90, or 100 culture plate wells.

Disclosed herein are methods comprising, for each of one or more partitioned surfaces or containers: a) selecting a cell based on its position on the partitioned surface or in the container, thereby identifying a selected cell, wherein the selecting is not based on whether the cell comprises an exogenous label or an expressed reporter; and b) photoablating non-selected cells on the partitioned surface or in the container, wherein at least 90% of the one or more partitioned surfaces or containers comprise only the selected cell as a viable cell after the photoablating is performed. In some embodiments, at least 95% of the one or more partitioned surfaces or containers comprise only the selected cell as the viable cell after the photoablating is performed. In some embodiments, at least 98% of the one or more partitioned surfaces or containers comprise only the selected cell as the viable cell after the photoablating is performed. In some embodiments, at least 99% of the one or more partitioned surfaces or containers comprise only one viable cell after the photoablating. In some embodiments, the one or more partitioned surfaces comprise at least 5, 10, 20, 30, 40, 50, 60, 70, 80, 90, or 100 partitioned surfaces. In some embodiments, each of the one or more partitioned surfaces comprise at least 5, 10, 20, 30, 40, 50, 60, 70, 80, 90, or 100 partitions.

In some embodiments, the one or more containers comprise at least 5, 10, 20, 30, 40, 50, 60, 70, 80, 90, or 100 containers. In some embodiments, the one or more partitioned surfaces or containers comprises one or more partitioned surfaces, wherein the selecting comprises selecting a cell based on its position on the one or more partitioned surfaces, wherein the photoablating comprises photoablating non-selected cells on the one or more partitioned surfaces, and wherein at least 90% of the one or more partitioned surfaces comprise only the selected cell as a viable cell after the photoablating is performed. In some embodiments, the one or more partitioned surfaces or containers comprises one or more containers, wherein the selecting comprises selecting a cell based on its position in the one or more containers, wherein the photoablating comprises photoablating non-selected cells in the one or more containers, and wherein at least 90% of the one or more containers comprise only the selected cell as a viable cell after the photoablating is performed. In some embodiments, the photoablating comprises use of a laser. In some embodiments, the non-selected cells are photoablated using light in the wavelength range of 1440 nm to 1450 nm.

Also disclosed are methods comprising: photoablating all but a first cell of two or more cells on a surface or in a container. In some embodiments, the photoablating comprises photoablating all but a first cell of two or more cells on a surface. In some embodiments, the photoablating comprises photoablating all but a first cell of two or more cells in a container. In some embodiments, the method further comprises growing a clonal population of the first cell after the photoabalating is performed. In some embodiments, the method further comprises photodetaching one or more cells of the clonal population from a growth surface. In some embodiments, the method further comprises testing the one or more photodetached cells. In some embodiments, the method further comprises performing an assay on the one or more photodetached cells. In some embodiments, the method further comprises selecting the first cell using an imaging technique. In some embodiments, the imaging technique comprises bright-field imaging, dark-field imaging, phase contrast imaging, fluorescence imaging, or any combination thereof. In some embodiments, the method further comprises selecting the first cell using an automated image analysis process. In some embodiments, the selecting is based on a proximity of the first cell to a center of the surface or the container. In some embodiments, the selecting is based on size of the first cell. In some embodiments, the selecting is based on morphology of the first cell. In some embodiments, the selecting is based on a phenotype of the first cell. In some embodiments, the selecting is based on a development stage of the first cell. In some embodiments, the selecting is based on one or more biomarkers. In some embodiments, the one or more biomarkers comprise a genetically-engineered protein. In some embodiments, the genetically-engineered protein comprises a green fluorescent protein (GFP) domain. In some embodiments, the one or more biomarkers comprise one or more cell surface receptors. In some embodiments, the one or more cell surface receptors are labeled with fluorescently-tagged antibodies that bind specifically to the one or more cell surface receptors. In some embodiments, the one or more biomarkers comprise fluorescent signals that are derived from one or more fluorescent probes of cellular metabolic state. In some embodiments, the selecting is based on detection of a CRISPR editing success parameter of the first cell. In some embodiments, the CRISPR editing success parameter comprises a Cas-dependent fluorescent moiety. In some embodiments, the Cas9-dependent fluorescent moiety is a Cas-GFP construct. In some embodiments, the photoablating comprises photoablating all but a first cell of two or more cells on a surface, and wherein the surface is a surface in a culture plate well. In some embodiments, the two or more cells comprise about 10 to about 15 cells. In some embodiments, the two or more cells consist of 10 to 15 cells. In some embodiments, the photoablating comprises photoablating at least 80% of five or more cells on the surface or in the container. In some embodiments, at least 90% of 9 of more cells on the surface or in the container are photoablated. In some embodiments, at least 95% of 20 or more cells on the surface or in the container are photoablated. In some embodiments, at least 99% of 99 or more cells on the surface or in the container are photoablated. In some embodiments, cells are photoablated at a rate of at least 60 cells per minute. In some embodiments, cells are photoablated with an efficiency of greater than 99%. In some embodiments, cells are photoablated using light in the wavelength range of 1440 nm to 1450 nm.

Disclosed herein are methods comprising photoablating at least 80% of five or more cells in a plurality of culture plate wells, wherein at least 95% of the plurality of culture plate wells contain only one viable cell after the photoablating is performed. In some embodiments, at least 98% of the plurality of culture plate wells contain only one viable cell after the photoablating is performed. In some embodiments, at least 99% of the plurality of culture plate wells contain only one viable cell after the photoablating is performed. In some embodiments, the plurality of culture plate wells comprises at least 5, 10, 20, 30, 40, 50, 60, 70, 80, 90, or 100 culture plate wells. In some embodiments, the photoablating comprises use of a laser. In some embodiments, cells are photoablated at a rate of at least 60 cells per minute. In some embodiments, cells are photoablated with an efficiency of greater than 99%. In some embodiments, cells are photoablated using light in the wavelength range of 1440 nm to 1450 nm.

Disclosed herein are methods comprising: a) providing cells in each of two or more partitioned surfaces or containers; b) selecting a cell in each partitioned surface or container to retain, thereby identifying a selected cell; and c) photoablating all of the cells in each partitioned surface or container except the selected cell, wherein cells are photoablated at a rate of at least 60 cells per second. In some embodiments, the two or more partitioned surfaces or containers comprise at least 5, 10, 20, 30, 40, 50, 60, 70, 80, 90, or 100 partitioned surfaces or containers. In some embodiments, the two or more partitioned surfaces comprise at least 5, 10, 20, 30, 40, 50, 60, 70, 80, 90, or 100 partitioned surfaces. In some embodiments, each of the two or more partitioned surfaces comprise at least 5, 10, 20, 30, 40, 50, 60, 70, 80, 90, or 100 partitions. In some embodiments, the two or more containers comprise at least 5, 10, 20, 30, 40, 50, 60, 70, 80, 90, or 100 containers. In some embodiments, the method further comprises growing a clonal population of the selected cell in at least one of the two or more partitioned surfaces or containers. In some embodiments, the method further comprises photodetaching one or more cells of the clonal population grown on or in the at least one partitioned surface or container. In some embodiments, the method further comprises testing the one or more photodetached cells. In some embodiments, the selecting comprises using an automated image analysis process. In some embodiments, the selecting is based on a proximity of the selected cell to a center of the partitioned surface or the container. In some embodiments, the selecting is based on size of the selected cell. In some embodiments, the selecting is based on morphology of the selected cell. In some embodiments, the selecting is based on phenotype of the selected cell. In some embodiments, the selecting is based on development stage of the selected cell. In some embodiments, the selecting is based on one or more biomarkers. In some embodiments, the one or more biomarkers comprise a genetically-engineered protein. In some embodiments, the genetically-engineered protein comprises a green fluorescent protein (GFP) domain. In some embodiments, the one or more biomarkers comprise one or more cell surface receptors. In some embodiments, the one or more cell surface receptors are labeled with fluorescently-tagged antibodies that bind specifically to the one or more cell surface receptors. In some embodiments, the one or more biomarkers comprise fluorescent signals that are derived from one or more fluorescent probes of cellular metabolic state. In some embodiments, the selecting is based on detection of a CRISPR editing success parameter. In some embodiments, the CRISPR editing success parameter comprises a Cas-dependent fluorescent moiety. In some embodiments, the Cas9-dependent fluorescent moiety is a Cas-GFP construct. In some embodiments, the photoablating comprises use of a laser. In some embodiments, cells are photoablated at a rate of at least 60 cells per minute. In some embodiments, cells are photoablated with an efficiency of greater than 99%. In some embodiments, cells are photoablated using light in the wavelength range of 1440 nm to 1450 nm.

Disclosed herein are systems for preparing clonal cell populations, the system comprising: a) an imaging system configured to image cells in each of one or more partitioned surfaces or containers; and b) a laser that is optically coupled to the imaging system; wherein the system is configured to perform any of the methods disclosed herein. In some embodiments, the system further comprises a translation stage configured to accurately position individual cells at a laser focal point on a sample plane of the imaging system so that individual cells can be photoablated or photodetached. In some embodiments, the system is configured to scan the laser relative to the one or more partitioned surfaces or containers so that individual cells can be photoablated or photodetached. In some embodiments, the imaging system is configured to image cells in each of one more containers, wherein the one or more containers are one or more culture plate wells, and wherein the system further comprises an incubator for maintaining the culture plate wells under a specified set of growth conditions. In some embodiments, the system further comprises a pick-and-place robot for moving culture plates between translation stage and the incubator. In some embodiments, the system further comprises a controller. In some embodiments, the controller is configured to provide manual, semi-automated, or fully-automated control of image acquisition. In some embodiments, the controller is configured to provide manual, semi-automated, or fully-automated control of image processing. In some embodiments, the controller is configured to provide manual, semi-automated, or fully-automated control of delivery of laser light to the sample plane of the imaging system. In some embodiments, the controller is configured to provide manual, semi-automated, or fully-automated control of positioning of individual cells at the laser focal point.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7A: a pattern of cells are destroyed by laser photoablation according to a specified set of position coordinates (box). FIG. 7B: a subsequent photoablation pattern performed on the same cell culture according to an updated set of position coordinates (box).

FIG. 8A: bright-field image of a cell culture plate showing three targeted single cells as indicated in the boxes. FIG. 8B: bright-field image of the same cell culture plate following the destruction of the targeted cells by laser photoablation.

DETAILED DESCRIPTION

Figure 1:
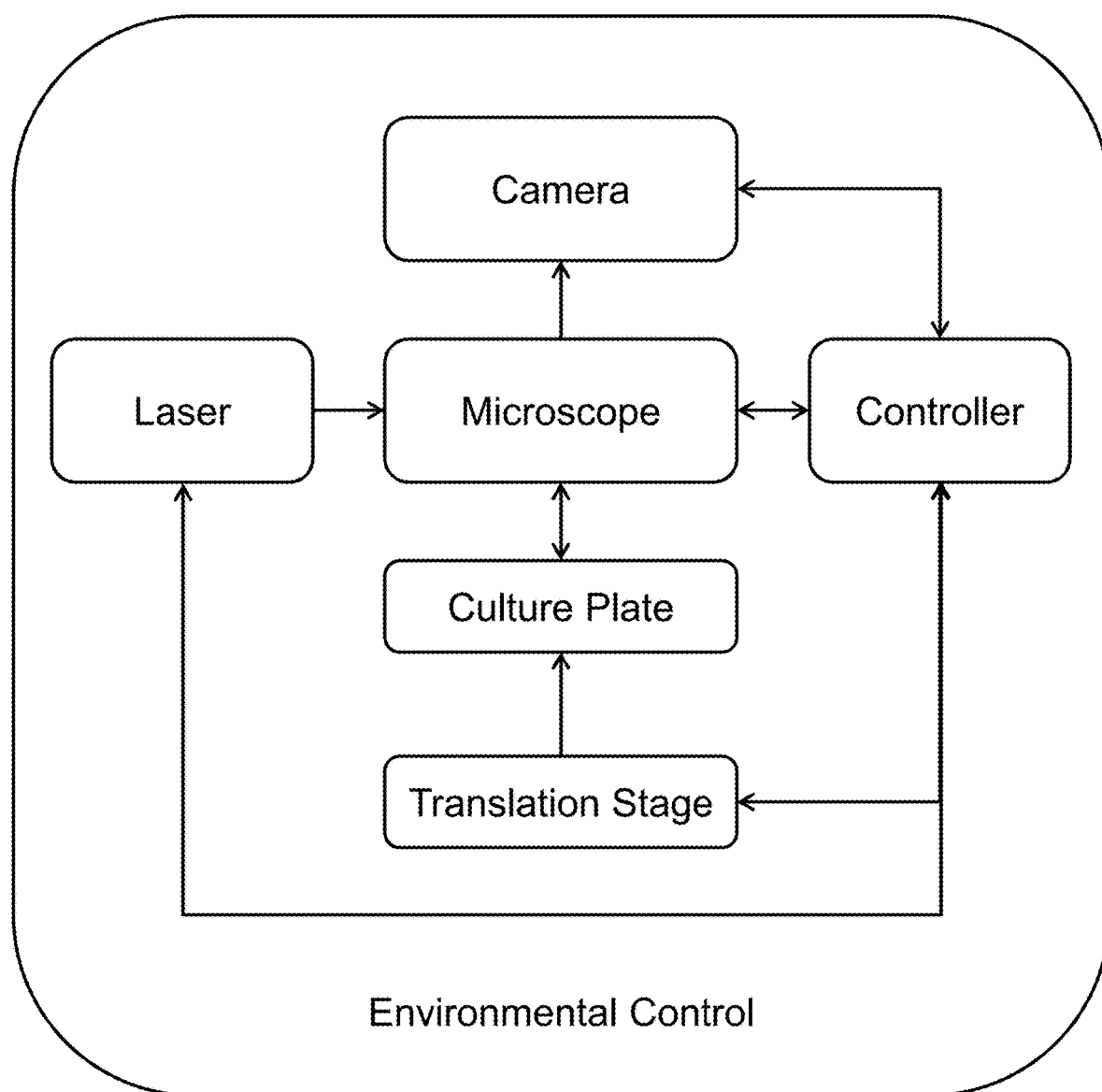
FIG. 1 provides a block diagram of a system for laser photoablation of cells in a cell culture according to one aspect of the present disclosure. In some instances, the system optionally comprises an environmental control chamber that encompasses the other system components. In some instances, the system controller may communicate with and control the environmental control chamber to maintain a specified temperature, humidity, $O_2$ concentration, $CO_2$ concentration, etc.

Disclosed herein are methods and systems for preparing clonal cell populations for which the confidence level that the cell population arose from a single cell is extremely high. The approach relies on the fact that the clone production process may start by using one or more surfaces or containers, e.g., culture plate wells, that each contain multiple cells as long as one has an efficient process for killing all but one of the cells (or in some instances, all but two or more cells to be retained). The one or more surfaces can be a surface of a container, e.g., a surface of a culture plate well, e.g., a bottom surface of an interior of a culture plate well. A combination of a microscope, image processing software for cell identification and position tracking, a translation stage, and a laser can be used to create a system for ablating unwanted cells on a surface or in a container, e.g., culture plate well, in which a number of cells, e.g., a relatively small number of cells, has first been deposited from a dilute cell suspension. Starting with one or more surfaces or containers, e.g., culture plate wells, that each comprise several cells can eliminate the problem inherent in trying to deposit single cells from a cell suspension that is sufficiently dilute to ensure that, according to the Poisson distribution, on average each surface or each container, e.g., a culture plate well, will contain only a single cell (i.e., that an excessive number of surfaces or containers, e.g., culture plate wells, will contain no cells at all), and allows one to use any of a variety of approaches for determining which cell (or, in some instances, a combination of cells) to keep. For example, in some instances, a single cell (or a combination of cells) may identified and retained purely on the basis of its location on a surface or within the container, e.g., culture plate well (e.g., its proximity to the center of the surface or container, e.g., well, e.g., bottom interior surface of the well, its proximity to the edge of the surface or container, e.g., well, e.g., surface of a well, or its proximity to any other defined position on the surface or within the container, e.g., well) without reference to cell-specific features. On the other hand, in some instances, a single cell (or a combination of cells) may be identified and retained based on one or more cell-specific criteria. Examples of criteria that may be used for selecting and retaining a cell (or for selecting and destroying a cell) include, but are not limited to, the total number of cells on a surface or in a container, e.g., well, cell phenotype, cell morphology, the presence of one or more specified biomarkers, and/or a reporter molecule status (e.g. the presence or absence of a green fluorescent protein (GFP) signal). In some cases, both features specific to a cell, and features not specific to a cell, are used to identify and/or select a cell for retention.

In general, the disclosed methods may comprise: (i) delivery of one or more cells, e.g., a cell suspension, e.g., a dilute cell suspension, onto one or more surfaces and/or into one or more containers, e.g., into one or more culture plate wells, so that a number of cells, e.g., a small number of cells (e.g., 5 to 10 cells) are deposited on each surface and/or in each container, e.g., in each well, (ii) imaging of each surface or container, e.g., culture plate well, (iii) processing of one or more images for each surface or container, e.g., culture plate well, to identify individual cells and determine their position on the surface or within the container, e.g., well, (iv) applying selection criteria to identify which one or more cells to retain and which to destroy, (v) programming the position coordinates of one or more unwanted cells into a targeting system which controls a translation stage and/or laser scanning system, and (vi) exposing the one or more unwanted cells on each surface or in each container, e.g., in each culture plate well, to laser light to destroy them using a photoablation process, wherein their successful destruction is recorded as part of the ablation process. In some instances, the disclosed methods may comprise any subset or any combination of these individual steps. In some instances, imaging of one or more surfaces or containers, e.g., culture plate wells, may comprise acquiring an image of a single field-of-view of the surface or within the container, e.g., well, wherein the single field-of-view comprises all or a portion of the surface or container, e.g., well. In some instances, imaging of one or more surfaces or containers, e.g., culture plate wells may comprise acquiring a tiled image created by stitching together two or more images which each comprise a different field-of-view of the surface or within the container, e.g., well. In some instances, in addition to identifying and locating individual cells on a surface or within a container, e.g., well, the image processing may be used to identify and locate doublets, triplets, or other aggregates of cells, which in some instances may be designated for ablation and in other instances, may be designated for retention. In some instances, any or all of the individual steps of the disclosed methods may be performed in a manual, semi-automated, or fully-automated fashion, as will be recognized by those of skill in the art.

Also disclosed herein are systems designed to perform the disclosed methods for preparing clonal cell populations. In general, the disclosed systems may comprise: (i) a microscope or other imaging system that is configured for viewing of one or more cells on a surface or in a container, e.g., culture dish, culture plate, culture container, or other cell culture format, (ii) a focusing system capable of re-focusing the microscope or imaging system on individual cells as necessary, (iii) a laser and objective that are capable of working in tandem to focus and deliver laser light to a specific location on a surface in a container, e.g., culture container, (iv) a camera or other image sensor that can be used to acquire images of one or more fields-of-view in each surface or container, e.g., culture plate well or culture container, (v) a translation stage capable of fast and accurate positioning of individual cells at the focal point of the objective, (vi) one or more processors, controllers, or computers, (vii) image capture and processing software for identifying cells and determining their position coordinates in each of a series of surfaces or containers, e.g., culture plate wells or culture containers, (viii) laser ablation control software for controlling laser power and/or exposure time, (ix) system control software for coordinating the image capture, image processing, translation stage movement, and laser ablation steps of the process, (x) an environmental control chamber or module that maintains the cells on the surfaces or in the containers, e.g., culture plates or culture containers, under a specified set of cell culture conditions, or (xi) any combination thereof. In some instances, a laser scanning system (e.g., comprising a micromirror array positioned in the optical path by which laser light is delivered to the sample plane of the microscope or imaging system) may be utilized instead of, or in addition to, a translation stage for focusing laser light onto individual cells. In some instances, the environmental chamber may encompass all or a portion of the remaining system components. In some instances, the environmental chamber may be configured to make contact with or encompass only the surface or container, e.g., cell culture containers being processed, e.g., it maybe sized and adapted to be mounted on the translation stage. In some instances, the system may further comprise a fluid handling system for depositing a specified volume of a cell suspension onto one or more surfaces or into each of one or more containers, e.g., culture plate wells or other culture containers, which may subsequently be transferred to the laser ablation system. In some instances, the system may further comprise robotics for moving the surfaces or containers, e.g., culture plates or culture containers, back and forth between the laser ablation system and long-term cell culturing incubators, along with control software that coordinates the robotic transfer of the surfaces or containers, e.g., culture plates or containers, with the image capture, image processing, translation stage movement, and laser ablation steps of the process. In some instances, the system may further comprise, e.g., barcode readers for tracking surfaces or containers, e.g., culture plates or culture containers, as they are moved in and out of the laser ablation system. In some instances, the system (or the computer, controller, or processor components thereof) may comprise a network interface for transferring surface or container, e.g., culture plate tracking data, image data, cell identification and ablation data, and/or other experimental data from the laser ablation system to a laboratory information management system (LIMS).

The disclosed methods and systems may be applied to any of a variety of emerging applications including, but not limited to, expression and purification of genetically-engineered proteins, nucleic acids, and other cellular components; production of biologic drugs (biologics); and therapeutic applications of stem cells. It shall be understood that different aspects of the disclosed methods and systems as described herein may be appreciated individually, collectively, or in combination with each other.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

An example of container may a culture plate or culture plate well. As used herein, a "culture plate" may refer to any of a variety of microplate-like devices comprising a substrate and well-forming component that divides the substrate into separate wells (or chambers, compartments, etc.). In some instances, a culture plate may comprise a microplate-like device that includes a lid or cover. In some instances the lid or cover may be removable or detachable. In some instances, a culture plate may be a petri dish. In some instances, a culture plate may comprise a substantially flat, planar substrate that has no well-forming component.

As used herein, the terms "laser photoablation", "photoablation", and simply "ablation" are used interchangeably and in a general sense to include various related mechanisms by which cells may be disrupted or destroyed upon exposure to light, e.g., intense light, at various wavelengths (ranging from ultraviolet (UV) wavelengths to infrared (IR) wavelengths) in either a pulsed or continuous wave mode.

Clonal cell culture preparation methods: The most time consuming and costly aspect of producing a clone can be isolation and expansion of a single cell. As noted above, existing methods for generating cell clones focus on isolating a single cell in a culture container (i.e., cell singulation) using any of a variety of techniques and technologies for separating the cell from a mixture of cells. Isolation of single cells may be carried out, for example, using a cell sorting device such as the WOLF cell sorter (Nanocellect Biomedical, Inc., San Diego, Calif.), the single cell printer (Cytena, GmbH, Freiburg, Germany), or the Yamaha Cell Picker (Yamaha, Inc.). There are many other examples of cell singulation devices (reviewed by Carey, et al. (2018), "Developments in label-free microfluidic methods for single-cell analysis and sorting", WIREs Nanomed Nanobiotechnol 112: e1529-17) and those technologies are all capable of isolating a single cell from other cells for culturing. However, all of these techniques passage cells through microfluidic features (<100 um in at least one dimension) that can subject a cell to mechanical stress that can decrease the fitness and viability of the cell.

The methods disclosed herein differ from the cell singulation approaches described in the previous paragraph in that they bypass the difficulties of depositing a single cell on a surface in a container, e.g., well, and instead focus on destroying unwanted cells, e.g., once they have settled on a surface or in a container, e.g., well. There are a number of automated processes that can deposit several cells (e.g., 5-10 cells) in 100% of the targeted culture plate wells. The disclosed methods for then efficiently removing the unwanted cells can provide for a much higher throughput and less costly clone production process.

As noted above, the disclosed methods may comprise all or a subset of the following steps: (i) delivery of cells, e.g., a cell suspension, e.g., a dilute cell suspension, onto one or more surfaces or into one or more containers, e.g., culture plate wells so that a small number of cells (e.g., 5 to 15 cells) are deposited on each surface or in each container, e.g., well, (ii) imaging of each surface or container, e.g., culture plate well, (iii) processing of one or more images for each surface or container, e.g., culture plate well to identify individual cells and determine their position within the well, (iv) applying selection criteria to identify which one or more cells to retain and which to destroy, (v) programming the position coordinates of one or more unwanted cells into a targeting system which controls a translation stage and/or laser scanning system, and (vi) exposing the one or more unwanted cells on each surface or in each container, e.g., culture plate well to laser light to destroy them using a photoablation process, wherein their successful destruction is recorded as part of the ablation process. In some instances, imaging of surfaces or containers, e.g., culture plate wells, may comprise acquiring an image of a single field-of-view of the surface or within the container, e.g., well, wherein the single field-of-view comprises all or a portion of the surface or the container, e.g., well. In some instances, imaging of surfaces or containers, e.g., culture plate wells may comprise acquiring a tiled image created by stitching together two or images which each comprise a different field-of-view of the surface or within the container, e.g., well. In some instances, in addition to identifying and locating individual cells on a surface or within a container, e.g., well, the image processing may be used to identify and locate doublets, triplets, or other aggregates of cells, which in some instances may be designated for ablation and in other instances, may be designated for retention. In some instances, any or all of the individual steps of the disclosed methods may be performed in a manual, semi-automated, or fully-automated fashion, as will be recognized by those of skill in the art.

Cells: The disclosed methods and systems may be used for preparation of clonal populations of any of a variety of cells known to those of skill in the art. In some aspects, the cells may be any adherent and non-adherent eukaryotic cell, mammalian cell, primary or immortalized human cell or cell line, primary or immortalized rodent cell or cell line, cancer cells, normal or diseased human cells derived from any of a variety of different organs or tissue types (e.g., white blood cells, red blood cells, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, small intestine), distinct cell subsets such as immune cells, CD8+ T cells, CD4+ T cells, $CD44^{high}/CD24^{low}$ cancer stem cells, $Lgr5/6^+$ stem cells, undifferentiated human stem cells, human stem cells that has been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts), animal cells (e.g., mouse, rat, pig, dog, cow, or horse), plant cells, yeast cells, fungal cells, bacterial cells, algae cells, adherent or non-adherent prokaryotic cells, or any combination thereof. In some aspects, the cells may be immune cells, e.g., T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, macrophages, or any combination thereof.

As noted, in some instances the disclosed methods and systems may be used to prepare clonal populations of stem cells, e.g., embryonic stem cells, adult (tissue-specific) stem cells, mesenchymal stem cells, or induced pluripotent stem cells. Embryonic stem cells are obtained from the inner cell mass of a blastocyst (a mainly hollow ball of cells that, in the human, forms three to five days after an egg cell is fertilized by a sperm), and are typically pluripotent, i.e., they can be used to generate any of the body's specialized cell types, but typically cannot generate support structures like the placenta and umbilical cord. Adult stem cells are multipotent, i.e., they can typically generate a few different cell types found in a specific tissue or organ. Mesenchymal stem cells (MSCs; also sometimes referred to as "stromal cells") are isolated from, e.g., bone marrow or the stroma (the connective tissue that surrounds other tissues and organs). MSCs derived from bone marrow or other tissues have been shown to be capable of making bone, cartilage and fat cells, although it is unclear if they are actual stem cells or what other types of cells they are capable of generating. Their characteristics appear to depend on what tissue they are isolated from and how they are isolated and grown.

In some instances, the disclosed methods and systems may be used to prepare clonal populations of induced pluripotent stem cells (IPSCs), or any differentiated cell line derived therefrom. Induced pluripotent stem cells are derived from, e.g., skin or blood cells that have been reprogrammed to regress into an embryonic-like pluripotent state, and which may subsequently be triggered to differentiate into any of a variety of specific cell types, e.g., beta islet cells, egg and sperm precursors, liver cells, bone precursor cells, blood cells, neurons, and the like, for use in biomedical research and/or therapeutic applications.

Cell deposition: The disclosed methods for preparation of clonal cell populations may comprise an initial step of depositing cells onto one or more surfaces or into one or more containers, e.g., culture plate wells or other culture containers. An objective can be to ensure that every container, e.g., well, contains at least one cell and preferably no more than several cells. In some cases, every container, e.g., culture plate well does not comprise at least one cell. Cells may be deposited using any of a variety of liquid-dispensing or plate-handling systems, e.g., liquid-dispensing and plate-handling robotic systems. The cell concentration in the stock cell suspension and/or the volume of liquid dispensed onto each surface into each container, e.g., well, can be adjusted so that on average each surface (e.g., partitioned surface) or container, e.g., well, comprises a desired number of cells, e.g., 5 to 10 cells. In some instances, each surface or container, e.g., well may contain, or may contain on average, at least 1 cell, at least 2 cells, at least 3 cells, at least 4 cells, at least 5 cells, at least 6 cells, at least 7 cells, at least 8 cells, at least 9 cells, at least 10 cells, at least 11 cells, at least 12 cells, at least 13 cells, at least 14 cells, at least 15 cells, at least 16 cells, at least 17 cells, at least 18 cells, at least 19 cells, at least 20 cells, at least 25 cells, at least 30 cells, at least 40 cells, or at least 50 cells. In some instances, each surface or container, e.g., well may contain, or may contain on average, at most 50 cells, at most 40 cells, at most 30 cells, at most 25 cells, at most 20 cells, at most 19 cells, at most 18 cells, at most 17 cells, at most 16 cells, at most 15 cells, at most 14 cells, at most 13 cells, at most 12 cells, at most 11 cells, at most 10 cells, at most 9 cells, at most 8 cells, at most 7 cells, at most 6 cells, at most 5 cells, at most 4 cells, at most 3 cells, at most 2 cells, or at most 1 cell. Any of the lower and upper values described in this paragraph may be combined to form a range included within the present disclosure; for example, each surface well may contain from about 3 cells to about 14 cells. Those of skill in the art will recognize that the number of cells on a surface or in a container, e.g., well, following the initial deposition may have any value within this range, e.g., about 7 cells on average.

Any of a variety of liquid-dispensing and/or plate-handling robotics may be utilized for the initial deposition of cells onto surfaces or into containers, e.g., culture plate wells or other culture containers. Examples include, but are not limited to, the liquid-dispensing and plate-handling robotic systems available from Agilent—Velocity 11 (Menlo Park, Calif.), Beckman Coulter Life Sciences (Indianapolis, Ind.), Hamilton (Reno, Nev.), Perkin Elmer (Waltham, Mass.), Tecan (Baldwin Park, Calif.), or BioTek (Winooski, Vt.). In some cases, a robotics system is not used to deposit cells onto a surface or into a container, e.g., a culture plate well. In some cases, a method provided herein comprises obtaining a surface or a container, e.g., a culture plate well, comprising one or more cells, without a user performing a cell deposition step.

Cell culturing conditions: In general, the cell culturing conditions used (growth medium, incubation temperature, humidity, $O_2$ concentration, $CO_2$ concentration, type of culture flask, dish, or plate, etc.) will vary depending on the type of cell clones being prepared. A suitable growth medium provides the essential nutrients (amino acids, carbohydrates, vitamins, minerals, etc.) required by the specific cell type being cultured, maintains the pH and osmotic pressure required by the specific cell type being cultured, and may further comprise growth factors, hormones, etc. The cells can be anchorage-dependent cells that can be cultured while attached to a solid or semi-solid substrate (adherent or monolayer culture). In some cases, the cells can be grown floating in the culture medium (suspension culture). In some instances, the disclosed methods and systems may be used to prepare clonal cultures of non-adherent cells that have been allowed to settle on the bottom of a container, e.g., a culture plate well or culture container (or on a growth substrate contained therein).

Imaging of cell cultures: Any of a variety of imaging techniques may be utilized as part of the disclosed methods and systems for preparing clonal cell cultures. Examples include, but are not limited to, bright-field, dark-field, phase contrast, fluorescence, and two-photon fluorescence imaging. In some instances, a super-resolution imaging technique may be used, e.g., super-resolution fluorescence imaging, which may allow images to be captured with a higher spatial resolution (e.g., 10-200 nm resolution) than that determined by the diffraction limit of light at the imaging wavelength. In some instances, greyscale images of cells deposited in culture plate wells may be acquired and used for cell identification and determination of cell position coordinates. In some instances, red-green-blue (RGB, or color) images of cells deposited in culture plate wells may be acquired and used for cell identification and determination of cell position coordinates. Examples of suitable imaging acquisition hardware and image processing software will be discussed in more detail below.

Cell detection and selection: In some instances, images may be viewed live by a skilled operator for identification of cells and manual control of a translation stage to bring each cell to be ablated into position at the focal point of the laser. Images can be captured and processed using a semi-automated or fully-automated process to perform one or more of the following steps: (i) image segmentation, (ii) feature extraction, (iii) cell identification and determination of position coordinates, (iv) cell selection, and (v) transfer of cell position coordinate data for cells selected for destruction to a targeting system that controls the position of the translation stage and laser exposure to selectively ablate unwanted cells.

In some instances, the selection of a single cell (or a subset of cells) to retain is made randomly and all other cells within the culture plate well or culture container are destroyed. In some instances, the selection of a single cell (or a subset of cells) to retain is made on the basis of selection criteria that are independent of traits or properties inherent to the cells themselves (e.g., the selecting is not based on whether the cell comprises an exogenous label or an expressed reporter). For example, in some instances, a cell is selected to be retained simply on the basis of its location on a surface within a container, e.g., culture plate well. In some instances, a cell (or a subset of cells) that is closest to the center of a surface or a container, e.g., culture plate well or culture container is selected to be retained, and all other cells are ablated. In some instances, a cell (or a subset of cells) that is a specified distance from the center of a surface or a container, e.g., a culture plate well or culture container is selected to be retained, and all other cells are ablated. In some instances, a cell (or a subset of cells) that is closest to a wall of a container, e.g., a culture plate well or culture container is selected to be retained, and all other cells are ablated. In some instances, cell doubles, triplets, or other aggregates of cells will be ablated regardless of their position on a surface or within a container, e.g., a culture plate well or culture container.

In some instances, the selection of a single cell (or a subset of cells) to retain (or destroy) is made on the basis of selection criteria that are dependent on traits or properties inherent to the cells themselves. For example, as noted above, criteria that may be used for selecting and retaining a cell (or for selecting and destroying a cell) include, but are not limited to, cell phenotype, cell morphology, cell size, development stage, the presence or absence of one or more specified biomarkers, and/or a reporter molecule status (e.g. the presence or absence of a green fluorescent protein (GFP) signal).

In some instances, the selection of a single cell (or a subset of cells) to retain (or destroy) is made on the basis of the presence or absence of one or more biomarkers comprising cell surface receptors and ligands, e.g., G-protein coupled receptors (GPCRs), enzyme-linked receptors, ion channel-linked receptors, membrane-based receptor tyrosine kinases, membrane glycoproteins, etc. Examples of cell surface receptors and ligands that may be used as a basis for cell selection include, but are not limited to, angiotensin receptors, CD1a-e, CD3, CD4, CD6, CD8a-b, CD19, CD20, CD22, CD33, CD52, FGF receptors, growth hormone receptor, the KCNE1 ion channel, the KCNQ1 ion channel, the ATP1G1 Mg transporter, etc. (see, for example, Várady, et al. (2013), "Cell surface membrane proteins as personalized biomarkers: where we stand and where we are headed", Biomarkers Med. 7(5), 803-819, for additional examples). In some instances, the presence or absence of one or more cell surface biomarkers may be detected using, e.g., one or more fluorescently-tagged antibodies that bind specifically to one of the biomarkers of interest.

In some instances, the selection of a single cell (or a subset of cells) to retain (or destroy) may be made on the basis of the presence or absence of one or more biomarkers comprising genetically-engineered proteins, e.g., chimeric receptors or enzymes comprise a green fluorescence protein (GFP) domain (or a domain from any variant of GFP). In some instances, the selection of a single cell (or a subset of cells) to retain (or destroy) may be made on the basis of the presence or absence of one or more chimeric proteins comprising a GFP domain in a cell line that has been engineered to express one or more GFP-containing proteins as part of a reporter system for detection of a change in cellular gene expression profiles (e.g., for the detection of an increase or decrease of the transcription and/or translation of a specific set of one or more genes). In some instances, the selection of a single cell (or subset of cells) to retain (or destroy) may be made on the basis of the presence or absence of one or more chimeric proteins comprising a GFP domain in a cell line that has been engineered to express one or more GFP-containing proteins as part of a reporter system for detection of a change in cellular gene expression profiles due to a CRISPR editing success parameter. In some instances, the CRISPR editing success parameter may comprise a Cas-dependent fluorescent moiety (e.g., a Cas9-dependent fluorescent moiety). In some instances, a deactivated Cas (dCAS) can be tagged with XFP and in combination with a guide be used to identify cells that have been edited (Ma, H. et al. (2015), "Multicolor CRISPR Labeling of Chromosomal Loci in Human Cells", Proc. Natl. Acad. Sci. USA 112, 3002-3007).

In some instances, the selection of a single cell (or a subset of cells) to retain (or destroy) may be made on the basis of the presence or absence of one or more biomarkers comprising fluorescent signals that are derived from one or more fluorescent probes of cellular metabolic state. Examples of fluorescent probes that may be used to monitor cellular metabolic state include, but are not limited to, the "BioTracker" (Sigma-Aldrich, St. Louis, Mo.) series of fluorescent dyes for discriminating between live cells and dead cells, fluorescent probes for intracellular calcium$^{2+}$ concentration (e.g., Fura 2 AM, Fura Red AM, Indo-1 AM, all from ThermoFisher Scientific, Waltham, Mass.), fluorescent probes for transmembrane potentials (e.g., FluoVolt Membrane Potential Dye, di-3-ANEPPDHQ, or bis-(1,3-dibutylbarbituric acid)trimethine oxonol ($DiBAC_4(3)$), all from ThermoFisher Scientific, Waltham, Mass.), etc.

Once one or more cells have been selected for retention using any of the approaches described above, the remaining unwanted cells are photoablated and the surface or container, e.g., culture plate or culture container, may be returned to a suitable incubator or cell culture chamber for growing clonal populations of the selected cells. In some cases, the one or more cells selected for retention are not cultured following ablation of unwanted cells. In some cases, the one or more cells selected for retention are transferred to another surface or container, e.g., following photoablation of one or more unwanted cells. In some cases, the one or more cells selected for retention are analyzed following photoablation of one or more unwanted cells, e.g., the one or more cells are subjected to single cell analysis, e.g., analysis of nucleic acids of single cell.

Photoablation methods: The disclosed methods and systems utilize laser photoablation (or simply "ablation") to selectively destroy one or more unwanted cells within a small plurality of cells on a surface or within a container, e.g., culture plate well or other culture container. As noted above, the term "photoablation" as used herein and as applied to the lysis and destruction of cells may refer to a variety of related techniques in which cells are subjected to an intense beam of light to selectively destroy single cells or groups of cells.

The disruption of cells can occur via a variety of different laser light—cell interaction mechanisms that are determined primarily by the irradiance within the focal volume (Zeigler and Chiu, (2009), "Laser Selection Significantly Affects Cell Viability Following Single-Cell Nanosurgery", Photochem. Photobiol. 85(5): 1218-1224). The mechanisms for optical disruption of cells may occur over a wide range of timescales from femtosecond (fsec) to continuous wave (cw), may comprise the use of any of a variety of lasers, and may comprise photothermal interactions, photoablation, or plasma-induced ablation (collectively referred to as "photoablation" herein). Photothermal interactions comprise the absorption of light by cells (or tags attached to said cells) that leads to local heating. Formally, photoablation can occur when absorption of a single photon by a molecule promotes an electron from a bonding to a nonbonding orbital, resulting in dissociation of the molecule. Photoablation may also result in a mechanical pressure wave radiating from the focal volume, a mechanism also known as cavitation. Plasma-induced ablation can be due to a multiphoton absorption process that results in the formation of a plasma, i.e., an ionized gas comprising positive ions and free electrons within the focal volume, which can minimize excess damage in nearby cells or tissues, and which may also lead to the formation of a cavitation bubble. Different mechanisms of laser-cell interaction may lead to significantly different outcomes for the targeted cell, e.g., to differences in cell viability. The experimental parameters that can determine which of these mechanisms dominate in cell disruption applications can be the duration of the laser pulse and its irradiance (Zeigler and Chiu, (2009), op. cit.).

In some instances of the disclosed methods and systems, the laser used for photoablation of cells may produce light at a peak wavelength ranging from about 220 nm (UV light) to about 1500 nm (IR light). In some instances, the peak wavelength of the laser light used for photoablation may be at least 220 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1,000 nm, at least 1,100 nm, at least 1,200 nm, at least 1,300 nm, at least 1,400 nm, or at least 1,500 nm. In some instances, the peak wavelength of the laser light used for photoablation may be at most 1,500 nm, at most 1,400 nm, at most 1,300 nm, at most 1,200 nm, at most 1,100 nm, at most 1,000 nm, at most 950 nm, at most 900 nm, at most 850 nm, at most 800 nm, at most 750 nm, at most 700 nm, at most 650 nm, at most 600 n, at most 550 nm, at most 500 nm, at most 450 nm, at most 400 nm, at most 350 nm, at most 300 nm, at most 250 nm, or at most 220 nm. Any of the lower and upper values described in this paragraph may be combined to form a range included within the present disclosure, for example, in some instances the peak wavelength of the laser light used for photoablation may range from about 1,300 nm to about 1,500 nm. Those of skill in the art will recognize that the peak wavelength of the laser light used for photoablation may have any value within this range, e.g., about 1,460 nm.

In some instances of the disclosed methods and systems, the laser used for photoablation of cells may produce light having a bandwidth (e.g., full width at half maximum (FWHM)) centered on or near the peak wavelength that ranges from about 0.0001 nm to about 10 nm, depending on peak wavelength and whether the laser is a continuous wave laser or pulsed laser. In some instances, the bandwidth may be at least 0.0001 nm, at least 0.001 nm, at least 0.01 nm, at least 0.1 nm, at least 1 nm, or at least 10 nm. In some instances, the bandwidth may be at most 10 nm, at most 1 nm, at most 0.1 nm, at most 0.01 nm, at most 0.001 nm, or at most 0.0001 nm. Any of the lower and upper values described in this paragraph may be combined to form a range included within the present disclosure, for example, in some instances the bandwidth may range from about 0.001 nm to about 1 nm. Those of skill in the art will recognize that the bandwidth of the laser light used for photoablation may have any value within this range, e.g., about 0.25 nm.

In some instances of the disclosed methods and systems, the laser used for photoablation of cells may produce continuous wave light, and an electro-optic modulator or electronic shutter may be used to create pulses of light of arbitrarily long duration (e.g., ranging from tens of picoseconds to seconds). In some instances of the disclosed methods and systems, the laser used for photoablation of cells may be a pulsed laser, and may produce light pulses having a duration ranging from about 1 femtosecond to about 100 milliseconds. In some instances, the light pulses used for photoablation may be at least 1 femtosecond, at least 1 picosecond, at least 1 nanosecond, at least 1 millisecond, at least 10 milliseconds, at least 100 milliseconds, or at least 1 second in duration. In some instances, the light pulses used for photoablation may be at most 1 second, at most 100 milliseconds, at most 10 milliseconds, at most 1 millisecond, at most 1 nanosecond, at most 1 picosecond, or at most 1 femtosecond in duration. Any of the lower and upper values described in this paragraph may be combined to form a range included within the present disclosure, for example, in some instances the light pulses used for photoablation may range from about 1 picosecond to about 1 nanosecond in duration. Those of skill in the art will recognize that the pulse duration of the laser light used for photoablation may have any value within this range, e.g., about 0.250 nanoseconds.

In some instances of the disclosed methods and systems, the laser light used for photoablation of cells may be pulsed at a pulse repetition frequency ranging from about 1 Hz to about 100 MHz, depending on the type of laser used. In instances, the pulse repetition frequency may be at least 1 Hz, at least 10 Hz, at least 100 Hz, at least 1 KHz, at least 10 KHz, at least 100 KHz, at least 1 MHz, at least 10 MHz, or at least 100 MHz. In some instances, the pulse repetition frequency may be at most 100 MHz, at most 10 MHz, at most 1 MHz, at most 100 KHz, at most 10 KHz, at most 1 KHz, at most 100 Hz, at most 10 Hz, or at most 1 Hz. Any of the lower and upper values described in this paragraph may be combined to form a range included within the present disclosure, for example, in some instances the pulse repetition rate may range from about 10 Hz to about 1 MHz. Those of skill in the art will recognize that the pulse repetition rate may have any value within this range, e.g., about 16.5 KHz.

In some instances, the laser light irradiance (i.e., the radiant flux (power) delivered per unit area of surface, as measured, e.g., in units of $W/cm^2$) may range from about 0.1 $W/cm^2$ to about $10^{10}$ $W/cm^2$, depending on the type of laser used and the size of the focal spot at the sample plane. In some instances, the radiant flux delivered to the sample surface may be at least 0.1 $W/cm^2$, at least 1 $W/cm^2$, at least 10 $W/cm^2$, at least 100 $W/cm^2$, at least 1,000 $W/cm^2$, at least $10^4$ $W/cm^2$, at least $10^5$ $W/cm^2$, at least $10^6$ $W/cm^2$, at least $10^7$ $W/cm^2$, at least $10^8$ $W/cm^2$, at least $10^9$ $W/cm^2$, or at least $10^{10}$ $W/cm^2$. In some instances, the radiant flux delivered to the sample surface may be at most at most $10^{10}$ $W/cm^2$, at most $10^9$ $W/cm^2$, at most $10^8$ $W/cm^2$, at most $10^7$ $W/cm^2$, at most $10^6$ $W/cm^2$, at most $10^5$ $W/cm^2$, at most $10^4$ $W/cm^2$, at most 1,000 $W/cm^2$, at most 100 $W/cm^2$, at most 10 $W/cm^2$, at most 1 $W/cm^2$, or at most 0.1 $W/cm^2$. Any of the lower and upper values described in this paragraph may be combined to form a range included within the present disclosure, for example, in some instances the radiant flux delivered to the sample surface may range from about 10 $W/cm^2$ to about 1,000 $W/cm^2$. Those of skill in the art will recognize that the radiant flux delivered to the sample surface may have any value within this range, e.g., about 0.8 $W/cm^2$.

In some instances of the disclosed methods and systems, unwanted cells may be photoablated at a rate ranging from about 10 cells per minute to about 200 cells per minute. In some instances, unwanted cells may be photoablated at a rate of at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, or at least 200 cells per minute. In some instances, unwanted cells may be photoablated at a rate of at most 200, at most 190, at most 180, at most 170, at most 160, at most 150, at most 140, at most 130, at most 120, at most 110, at most 100, at most 90, at most 80, at most 70, at most 60, at most 50, at most 40, at most 30, at most 20, or at most 10 cells per minute. Any of the lower and upper values described in this paragraph may be combined to form a range included within the present disclosure, for example, in some instances unwanted cells may be photoablated at a rate ranging from about 50 cells per minute to about 180 cells per minute. Those of skill in the art will recognize that the photoablation rate may have any value within this range, e.g., about 64 cells per minute.

In some instances of the disclosed methods and systems, multiple surfaces or containers, e.g., culture plate wells (or other culture containers (or partitions in a partitioned surface)) may be processed (i.e., all unwanted cells in the surface or container, e.g., culture plate well or other culture container/partition, are destroyed using the disclosed photoablation methods) at a rate ranging from about 4 wells per minute to about 20 wells per minute. In some instances, culture plate wells may be processed at a rate of at least 4, at least 6, at least 8, at least 10, at least 12, at least 14, at least 16, at least 18, or at least 20 wells per minute. In some instances, culture plate wells may be processed at a rate of at most 20, at most 18, at most 16, at most 14, at most 12, at most 10, at most 8, at most 6, or at most 4 wells per minute. Any of the lower and upper values described in this paragraph may be combined to form a range included within the present disclosure, for example, in some instances culture plate wells may be processed at a rate ranging from about 6 wells per minute to about 18 wells per minute. Those of skill in the art will recognize that the rate at which culture plate wells are processed may have any value within this range, e.g., about 15 wells per minute.

In some instances of the disclosed methods and systems, the photoablation step may comprise ablating between about 80% and about 99% of the cells in a container, e.g., culture plate well (or other culture containers (or partitions in a partitioned surface)). In some instances, at least 80%, 85%, 90%, 95%, 98%, 99%, or 99.5% of the cells on a surface or in a container, e.g., culture plate well are photoablated, where the number of cells initially on the surface contained or in the container, e.g., well is at least 5, at least 10, at least 20, at least 30, at least 40, at least 50, at least 60, at least 70, at least 80, at least 90, at least 100, at least 125, at least 150, at least 175, at least 200 cells, at least 300 cells, at least 400 cells, or at least 500 cells. Any combination of ablation percentages and number of cells initially on a surface or contained in a container, e.g., culture plate well or other culture container described above is included in the present disclosure.

In some instances of the disclosed methods and systems, the efficiency of the photoablation reaction in rendering the cells selected for destruction as non-viable ranges from about 90% to about 99.99%, or higher. In some instances, the efficiency of the photoablation step is at least 90%, at least 95%, at least 96%, at least 97%, at least 98%, at least 99%, at least 99.5%, at least 99.6%, at least 99.7%, at least 99.8%, at least 99.9%, or at least 99.99%. In some instances, the efficiency of the photoablation step is at most 99.99%, at most 99.9%, at most 99.8%, at most 99.7%, at most 99.6%, at most 99.5%, at most 99%, at most 98%, at most 97%, at most 96%, at most 95%, or at most 90%. Any of the lower and upper values described in this paragraph may be combined to form a range included within the present disclosure, for example, in some instances the efficiency of the photoablation step may range from about 95% to about 99.8%. Those of skill in the art will recognize that the efficiency of the photoablation step may have any value within this range, e.g., about 99.85%.

In some instances of the disclosed methods and systems, the efficiency of the photoablation step is such that the percentage of containers, e.g., culture plate wells (or other culture containers or partitions of a partitioned surface) that retain a single viable cell ranges from about 90% to about 99.99%, or higher. In some instances, the percentage of processed containers, e.g., culture plate wells that retain a single viable cell is at least 90%, at least 95%, at least 96%, at least 97%, at least 98%, at least 99%, at least 99.5%, at least 99.6%, at least 99.7%, at least 99.8%, at least 99.9%, or at least 99.99%. In some instances, the percentage of processed containers, e.g., culture plate wells that retain a single viable cell is at most 99.99%, at most 99.9%, at most 99.8%, at most 99.7%, at most 99.6%, at most 99.5%, at most 99%, at most 98%, at most 97%, at most 96%, at most 95%, or at most 90%. Any of the lower and upper values described in this paragraph may be combined to form a range included within the present disclosure, for example, in some instances the percentage of processed culture plate wells that retain a single viable cell may range from about 95% to about 99.8%. Those of skill in the art will recognize that the percentage of processed containers, e.g., culture plate wells that retain a single viable cell may have any value within this range, e.g., about 99.74%.

Photodetachment methods: In some instances of the disclosed methods and systems, the same laser used for performing photoablation, or a different laser, may optionally be configured for performing photodetachment of cells from a surface on which they are growing rather than photoablation. Photodetachment may be used, for example, to detach and retrieve selected cells for subsequent testing (e.g., genetic testing) and/or culturing in a secondary culture plate or culture container.

Laser-based photodetachment offers a non-lethal means to dissociate adherent cells from a substrate on which they are grown without requiring chemical dissociation reagents. Adjustments to power settings, pulse-width modulation, and focal plane of the laser can be adjusted in such a way to create an energy pulse that effectively detaches the selected cells without destroying the cell membranes.

Focused laser light may, for example, be scanned across a region beneath or adjacent to one or more selected cells to detach the cells from a surface on which they are growing. In some instances, illumination by the focused laser light may result in a photothermal detachment of the one or more selected cells. In some instances, illumination by the focused laser light may result in a photomechanical detachment of the one or more selected cells. In some instances, illumination by the focused laser light may result in a photoacoustic detachment of the one or more selected cells. In some instances, the cell culture plate or culture container may comprise one or more surface coating layers that have been specially formulated to facilitate detachment of cells growing thereon by means of a photothermal and/or photomechanical detachment mechanism. In some instances, the cell culture plate or culture container may comprise one or more surface coating layers that comprise a photocleavable linker which tethers a cell recognition element, e.g., an antibody directed towards a cell surface receptor, to a surface within the cell selection compartment, where the cell recognition element is used to capture and tether suspension cells to a surface and where, upon illumination by focused laser light of the appropriate wavelength, the photocleavable linker is disrupted and a set of selected cells may be released from the surface.

Under static conditions, cells that have been detached may settle back down on the growth surface within the culture plate or container. In some instances, laser-based photodetachment may thus be performed in conjunction with providing a directed flow of fluid across the growth surface to direct the detached cells towards, e.g., a cell removal port through which they may be withdrawn from the cell culture device. The combination of laser-based photodetachment and flow-directed removal of detached cells allows one to remove targeted cells without risking contamination through manual intervention (e.g., through the use of media changes or chemical dissociation reagents).

In some instances, one or more lasers may be used for performing laser-induced photodetachment. In some instances, photodetachment may be performed using lasers operating in the ultraviolet (UV), visible, or near-infrared (near-IR) regions of the electromagnetic spectrum. In some instances, laser photodetachment may be performed using laser light in a wavelength range of about 1440 nm to about 1450 nm.

In some instances, one or more of the lasers used for photodetachment (or for photoablation) may be continuous wave lasers. In some instances, one or more of the lasers used for photodetachment (or for photoablation) may be pulsed lasers. Depending on the type of laser selected and the technique used to generate pulses (e.g., mode-locked solid-state laser, Q-switched solid-state laser, or gain switched semiconductor laser), laser pulse frequencies may range from less than 1 Hz to greater than 100 GHz. Similarly, depending on the type of laser selected and the technique used to generate pulses, laser pulse widths may range from longer than 1 microsecond to fewer than 100 femtoseconds.

In some instances, the same one or more lasers may be used to perform photodetachment and/or photoablation. In some instances, different lasers may be used to perform photodetachment, and/or photoablation. In the case that the same laser or set of lasers is used to perform photodetachment and/or photoablation, the system used in conjunction with the disclosed methods and culture plates or containers may be operably switched between a a photodetachment operating mode and a photoablation operating mode by controlling laser spot size, laser spot shape, laser light intensity, laser pulse frequency, laser pulse energy, the total number of laser pulses delivered at a specified position on a surface or within the volume of the cell culture plate or culture container, the position of the laser focal point relative to the surface or within the volume of the cell culture plate or cell culture container, or any combination thereof.

In some instances, the efficiency of laser-induced photodetachment may range from about 50% to about 100%. In some instances, the efficiency of laser-induced photodetachment may be at least 50%, at least 60%, at least 70%, at least 80%, at least 85%, at least 90%, at least 95%, at least 98%, at least 99%, or about 100%. In some instances, the efficiency of laser-induced photodetachment may be at most 100%, at most 99%, at most 98%, at most 95%, at most 90%, at most 85%, at most 80%, at most 70%, at most 60%, or at most 50%. Any of the lower and upper values described in this paragraph may be combined to form a range included within the present disclosure, for example, in some instances the efficiency of laser-induced photodetachment may range from about 60% to about 95%. Those of skill in the art will recognize that the efficiency of laser-induced photodetachment may have any value within this range, e.g., about 93%.

Cell removal and testing: In some instances, cells that have been detached from a growth surface within a cell culture plate or culture container may optionally be removed from the cell culture device and subjected to further testing. Examples of testing (or assays) to which the one or more cells removed from the cell culture plate or culture container may be subjected to include, but are not limited to, nucleic acid sequencing, gene expression profiling, detection of a modified RNA molecule, DNA molecule, or gene, detection of a CRISPR edited gene, a restriction site analysis of nucleic acid molecules, detection of a protein (e.g., a specific biomarker protein, a mutant protein, a reporter protein, or a genetically-engineered protein, and the like), detection of a change in an intracellular signaling pathway due to an altered protein function.

In some instances, the testing may be performed on a single cell that has been detached from a clonal cell colony and removed from the cell culture device. In some instances, the number of cells (e.g., the subset of cells that have been detached and removed from a single clonal cell colony) that are removed from the device for each clonal cell colony selected for testing may be fewer than 200 cells, fewer than 100 cells, fewer than 50 cells, fewer than 40 cells, fewer than 30 cells, fewer than 20 cells, fewer than 10 cells, or fewer than 5 cells.

System & system components: Disclosed herein are systems configured to perform the methods described above. As noted above, in some instances the disclosed systems may comprise (i) a microscope or other imaging system that is configured for viewing of cells on a surface or in a container, e.g., culture dish, culture plate, culture container, or other cell culture format, (ii) a focusing system capable of re-focusing the microscope or imaging system on individual cells as necessary, (iii) a laser and objective that are capable of working in tandem to focus and deliver laser light to a specific location in a culture container, (iv) a camera or other image sensor that can be used to acquire images of one or more fields-of-view on each surface or in each container, e.g., culture plate well or culture container, (v) a translation stage capable of fast and accurate positioning of individual cells at the focal point of the objective, (vi) one or more processors, controllers, or computers, (vii) image capture and processing software for identifying cells and determining their position coordinates in each of a series of containers, e.g., culture plate wells or culture containers, (viii) laser ablation control software for controlling laser power and/or exposure time, (ix) system control software for coordinating the image capture, image processing, translation stage movement, and laser ablation steps of the process, (x) an environmental control chamber or module that maintains the cells on the surface or in the containers, e.g., culture plates or culture containers under a specified set of cell culture conditions, or (xi) any combination thereof.

In some instances, a laser scanning system (e.g., comprising a micromirror array positioned in the optical path by which laser light is delivered to the sample plane of the microscope or imaging system) may be utilized instead of, or in addition to, a translation stage for focusing laser light onto individual cells. In some instances, the environmental chamber may encompass all or a portion of the remaining system components. In some instances, the environmental chamber may be configured to make contact with or encompass only the surfaces or containers, e.g., cell culture containers being processed, e.g., it maybe sized and adapted to be mounted on the translation stage. In some instances, the system may further comprise a fluid handling system for depositing a specified volume of a cell suspension into each of one or more surfaces or containers, e.g., culture plate wells or other culture containers, which may subsequently be transferred to the laser ablation system. In some instances, the system may further comprise robotics (e.g., plate-handling robotics or pick-and-place robotics) for moving surfaces or containers, e.g., culture plates or culture containers, back and forth between the laser ablation system and long-term cell culturing incubators, along with control software that coordinates the robotic transfer of surfaces of containers, e.g., culture plates or culture containers with the image capture, image processing, translation stage movement, and laser ablation steps of the process. In some instances, the system may further comprise, e.g., barcode readers for tracking surfaces or container, e.g., culture plates or culture containers, as they are moved in and out of the laser ablation system. In some instances, the system (or the computer, controller, or processor components thereof) may comprise a network interface for transferring container, e.g., culture plate tracking data, image data, cell identification and ablation data, and/or other experimental data from the laser ablation system to a laboratory information management system (LIMS).

Figure 2:
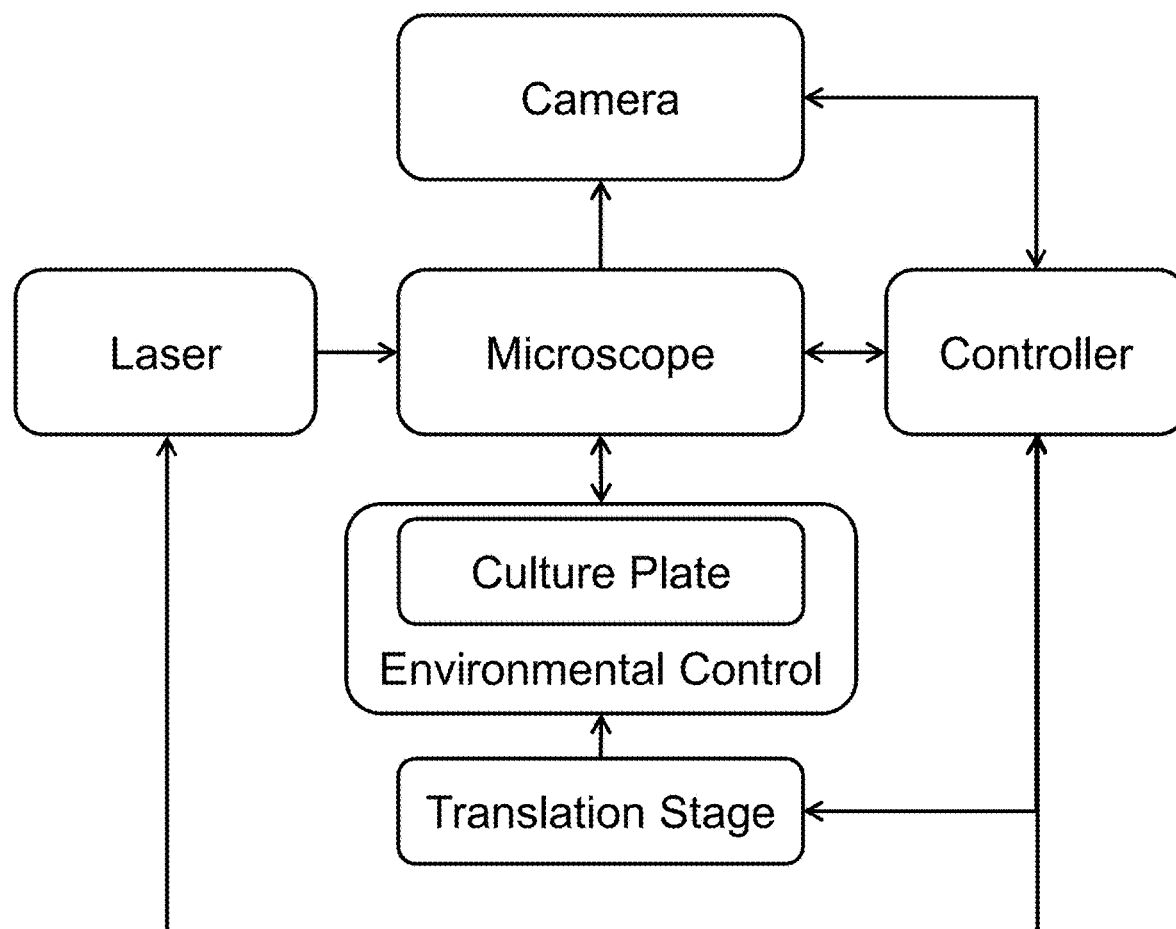
FIG. 2 provides a block diagram of a system for laser photoablation of cells in a cell culture according to one aspect of the present disclosure. In some instances, the system optionally comprises an environmental control chamber or module that resides on the microscope stage and makes contact with or fully- or partially-encompasses the culture plate. In some instances, the system controller may communicate with and control the environmental control chamber or module to maintain a specified temperature, humidity, CO2 concentration, etc.

FIG. 1 provides a schematic illustration of one non-limiting example of a system of the present disclosure. The system may comprise a microscope and camera (e.g., a CMOS or CCD camera) configured to capture images of an individual well of a container, e.g., culture plate (or other culture container) positioned at the focal plane for the microscope and at the focal point of a beam of laser light introduced via the microscope optics. In some instances, the system may comprise an autofocus module that re-focuses the microscope on a surface (e.g., a growth medium surface) within a culture plate well or container upon repositioning of the culture plate or container using a translation stage. In some instances, the control of the translation stage and positioning of the container, e.g., culture plate well, capture of images, selection of cells for ablation, and control of laser light exposure may be performed in a manual, semi-automated, or fully-automated manner. In some instances, a controller may execute a program comprising software-encoded instructions for coordinating and controlling the positioning of the translation stage, the capture of images, automated processing of images to identify cells and select a subset of cells for ablation, repositioning of the translation stage to target the selected subset of cells for exposure to laser light, and/or the exposure of cells to laser light, or any combination thereof. In some instances, as illustrated in FIG. 1, the entire laser ablation system may be housed within an environmental control chamber that excludes room light and/or provides control of environmental parameters such as temperature, humidity, $O_2$ concentration, $CO_2$ concentration, etc. In some instances, as illustrated in FIG. 2, the environmental control chamber may encompass only the container, e.g., culture plate being processed, or a stack of containers, e.g., culture plates ready to be processed.

Microscope or imaging system: In some instances, the disclosed systems may comprise a microscope equipped with a camera (or a custom imaging module) configured to capture images of containers, e.g., culture plate wells or other culture containers (including partitions on a partitioned surface). In some instances, the microscope may comprise a commercially-available microscope system, e.g., an upright, inverted, or epifluorescence microscope. In some instances, the microscope or imaging module may comprise one or more cameras or image sensors, light sources, objective lenses, additional lenses, prisms, diffraction gratings, mirrors, optical filters, colored glass filters, narrowband interference filters, broadband interference filters, dichroic reflectors, optical filters, apertures, optical fibers, optical waveguides, and the like, or any combination thereof.

In some instances, the microscope or imaging module of the disclosed systems may comprise an autofocus mechanism that re-focuses the microscope or imaging module on a surface (e.g., a growth medium surface or the bottom of a well) within a container, e.g., culture plate well, upon repositioning of the culture plate using a translation stage.

Any of a variety of light sources may be used to provide the imaging or excitation light, including but not limited to, tungsten lamps, tungsten-halogen lamps, arc lamps, lasers, light emitting diodes (LEDs), or laser diodes. In some instances, a combination of one or more light sources, and additional optical components, e.g. lenses, filters, apertures, diaphragms, mirrors, and the like, will comprise an illumination sub-system.

Any of a variety of image sensors may be used for imaging purposes, including but not limited to, charge-coupled device (CCD) cameras or sensors, image intensified CCD cameras or sensors, CMOS image cameras or sensors, and the like. In some instances, a combination of one or more image sensors, and additional optical components, e.g. lenses, filters, apertures, diaphragms, mirrors, and the like, will comprise an imaging sub-system.

Imaging mode: Any of a variety of imaging modes may be utilized in implementing the disclosed methods. Examples include, but are not limited to, bright-field imaging, dark-field imaging, phase contrast imaging, fluorescence imaging, super-resolution fluorescence imaging, two-photon fluorescence imaging, and the like. In some instances, dual wavelength excitation and emission (or multi-wavelength excitation or emission) fluorescence imaging may be performed.

In some instances, each surface or container, e.g., culture plate well (or culture container) may be imaged in its entirety within a single image, i.e., the field-of-view (FOV) may encompass the entire well, depending on the magnification used. In some embodiments, a series of images comprising a smaller FOV may be "tiled" or "stitched" to create a high-resolution image of the entire surface or container, e.g., well. In some instances, a series of one or more images may be acquired of all or a portion of a surface or container, e.g., culture plate well. In some instances, a series of two or more images may comprise images acquired both before and after performing the ablation step to destroy unwanted cells. In some instances, one or more images acquired after performing the ablation step may be used to confirm that the selected cell(s) have been destroyed. In some instanced, a series of images may comprise 1, 2, 3, 4, 5, 10, 15, 20, 30, 40, 50, 60, 70, 80, 90, or 100 or more images.

Image processing: In some instances of the disclosed methods and systems, image pre-processing and/or image processing may be performed in a manual, semi-automated, or fully-automated manner. In some instances, a series of one or more images may be pre-processed to, for example, correct image contrast and brightness, correct for non-uniform illumination, correct for an optical aberration (e.g., a spherical aberration, a chromatic aberration, etc.), remove noise, etc., or any combination thereof. In some instances, a series of one or more images may be processed to, for example, identify objects (e.g., cells or sub-cellular structures) within each of the images, segment each of the images to isolate the identified objects, tile segmented images to create composite images, perform feature extraction (e.g., identification and/or quantitation of object properties such as observable cellular phenotypic traits), determining the position coordinates for one or more selected cells, determining a confidence level for the destruction of the selected cells from one or more images acquired after performing the ablation step, or any combination thereof.

Any of a variety of image processing methods known to those of skill in the art may be used for image processing to identify objects within the images. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), image texture analysis methods (e.g., gray-level co-occurrence matrices), and mathematical analysis algorithms (e.g., Fourier transform, fast Fourier transform, wavelet analysis, auto-correlation, etc.), or any combination thereof.

Photoablation and/or photodetachment laser(s): Any of a variety of lasers may be used for photoablation and/or photodetachment purposes. Examples include, but are not limited to, diode (or semiconductor) lasers, solid-state lasers, gas lasers, and excimer lasers. Diode lasers can provide compact, relatively low power light sources that are available for a variety of wavelengths. Solid state lasers can have lasing material distributed in a solid matrix, e.g., the ruby or neodymium-YAG (yttrium aluminum garnet) lasers. The neodymium-YAG laser can emit infrared light at 1.064 micrometers. Gas lasers, e.g., helium and helium-neon (HeNe) lasers can have a primary output of visible red light. $CO_2$ lasers can emit energy in the far-infrared (10.6 micrometers) and can be used for cutting hard materials. Excimer lasers can use reactive gases such as chlorine and fluorine mixed with inert gases such as argon, krypton, or xenon which, when electrically stimulated produce a pseudomolecule or dimer, and when lased produce light in the ultraviolet wavelength range.

As noted above, the laser used for photoablation and/or photodetachement of cells in the disclosed methods and systems may produce light at a peak wavelength ranging from about 220 nm (UV light) to about 1500 nm (IR light). In some instances, the peak wavelength of the laser light used for photoablation and/or photodetachment may be at least 220 nm, at least 250 nm, at least 300 nm, at least 350 nm, at least 400 nm, at least 450 nm, at least 500 nm, at least 550 nm, at least 600 nm, at least 650 nm, at least 700 nm, at least 750 nm, at least 800 nm, at least 850 nm, at least 900 nm, at least 950 nm, at least 1,000 nm, at least 1,100 nm, at least 1,200 nm, at least 1,300 nm, at least 1,400 nm, or at least 1,500 nm. In some instances, the peak wavelength of the laser light used for photoablation and/or photodetachment may be at most 1,500 nm, at most 1,400 nm, at most 1,300 nm, at most 1,200 nm, at most 1,100 nm, at most 1,000 nm, at most 950 nm, at most 900 nm, at most 850 nm, at most 800 nm, at most 750 nm, at most 700 nm, at most 650 nm, at most 600 n, at most 550 nm, at most 500 nm, at most 450 nm, at most 400 nm, at most 350 nm, at most 300 nm, at most 250 nm, or at most 220 nm. Any of the lower and upper values described in this paragraph may be combined to form a range included within the present disclosure, for example, in some instances the peak wavelength of the laser light used for photoablation and/or photodetachment may range from about 1,300 nm to about 1,500 nm. Those of skill in the art will recognize that the peak wavelength of the laser light used for photoablation and/or photodetachment may have any value within this range, e.g., about 1,460 nm.

As noted above, in some instances the laser used for photoablation and/or photodetachment of cells in the disclosed methods and systems may produce light having a bandwidth (e.g., full width at half maximum (FWHM)) centered on or near the peak wavelength that ranges from about 0.0001 nm to about 10 nm, depending on peak wavelength and whether the laser is a continuous wave laser or pulsed laser. In some instances, the bandwidth may be at least 0.0001 nm, at least 0.001 nm, at least 0.01 nm, at least 0.1 nm, at least 1 nm, or at least 10 nm. In some instances, the bandwidth may be at most 10 nm, at most 1 nm, at most 0.1 nm, at most 0.01 nm, at most 0.001 nm, or at most 0.0001 nm. Any of the lower and upper values described in this paragraph may be combined to form a range included within the present disclosure, for example, in some instances the bandwidth may range from about 0.001 nm to about 1 nm. Those of skill in the art will recognize that the bandwidth of the laser light used for photoablation and/or photodetachment may have any value within this range, e.g., about 0.25 nm.

As noted above, in some instances the laser used for photoablation and/or photodetachment of cells in the disclosed methods and systems may produce continuous wave light, and an electro-optic modulator or electronic shutter may be used to create pulses of light of arbitrarily long duration (e.g., ranging from tens of picoseconds to seconds). In some instances of the disclosed methods and systems, the laser used for photoablation and/or photodetachment of cells may be a pulsed laser and may produce light pulses having a duration ranging from about 1 femtosecond to about 100 milliseconds. In some instances, the light pulses used for photoablation and/or photodetachment may be at least 1 femtosecond, at least 1 picosecond, at least 1 nanosecond, at least 1 millisecond, at least 10 milliseconds, at least 100 milliseconds, or at least 1 second in duration. In some instances, the light pulses used for photoablation and/or photodetachment may be at most 1 second, at most 100 milliseconds, at most 10 milliseconds, at most 1 millisecond, at most 1 nanosecond, at most 1 picosecond, or at most 1 femtosecond in duration. Any of the lower and upper values described in this paragraph may be combined to form a range included within the present disclosure, for example, in some instances the light pulses used for photoablation and/or photodetachment may range from about 1 picosecond to about 1 nanosecond in duration. Those of skill in the art will recognize that the pulse duration of the laser light used for photoablation and/or photodetachment may have any value within this range, e.g., about 0.250 nanoseconds.

As noted above, in some instances, the laser light used for photoablation and/or photodetachment of cells in the disclosed methods and systems may be pulsed at a pulse repetition frequency ranging from about 1 Hz to about 100 MHz, depending on the type of laser used. In instances, the pulse repetition frequency may be at least 1 Hz, at least 10 Hz, at least 100 Hz, at least 1 KHz, at least 10 KHz, at least 100 KHz, at least 1 MHz, at least 10 MHz, or at least 100 MHz. In some instances, the pulse repetition frequency may be at most 100 MHz, at most 10 MHz, at most 1 MHz, at most 100 KHz, at most 10 KHz, at most 1 KHz, at most 100 Hz, at most 10 Hz, or at most 1 Hz. Any of the lower and upper values described in this paragraph may be combined to form a range included within the present disclosure, for example, in some instances the pulse repetition rate may range from about 10 Hz to about 1 MHz. Those of skill in the art will recognize that the pulse repetition rate may have any value within this range, e.g., about 16.5 KHz.

In some instances, the laser light irradiance (i.e., the radiant flux (power) delivered per unit area of surface, as measured, e.g., in units of $W/cm^2$) may range from about 0.1 $W/cm^2$ to about $10^{10}$ $W/cm^2$, depending on the type of laser used and the size of the focal spot at the sample plane. In some instances, the radiant flux delivered to the sample surface may be at least 0.1 $W/cm^2$, at least 1 $W/cm^2$, at least 10 $W/cm^2$, at least 100 $W/cm^2$, at least 1,000 $W/cm^2$, at least $10^4$ $W/cm^2$, at least $10^5$ $W/cm^2$, at least $10^6$ $W/cm^2$, at least $10^7$ $W/cm^2$, at least $10^8$ $W/cm^2$, at least $10^9$ $W/cm^2$, or at least $10^{10}$ $W/cm^2$. In some instances, the radiant flux delivered to the sample surface may be at most at most $10^{10}$ $W/cm^2$, at most $10^9$ $W/cm^2$, at most $10^8$ $W/cm^2$, at most $10^7$ $W/cm^2$, at most $10^6$ $W/cm^2$, at most $10^5$ $W/cm^2$, at most $10^4$ $W/cm^2$, at most 1,000 $W/cm^2$, at most 100 $W/cm^2$, at most 10 $W/cm^2$, at most 1 $W/cm^2$, or at most 0.1 $W/cm^2$. Any of the lower and upper values described in this paragraph may be combined to form a range included within the present disclosure, for example, in some instances the radiant flux delivered to the sample surface may range from about 10 $W/cm^2$ to about 1,000 $W/cm^2$. Those of skill in the art will recognize that the radiant flux delivered to the sample surface may have any value within this range, e.g., about 0.8 $W/cm^2$.

In some instances, the disclosed systems may comprise two or more lasers operating in parallel (e.g., wherein the two laser beams are delivered to the sample plane via the same objective, but where they comprise different optical paths leading into or through the microscope or imaging module so that they can be individually targeted to different pairs of position coordinates) such that two or more cells may be ablated in parallel. In some instances, the laser light provided by a single laser may be divided into two or more beams that are delivered to the sample plane via the same objective, but where different optical paths leading into or through the microscope or imaging module are used so that the divided beams can be individually targeted to different pairs of position coordinates) such that two or more cells may be ablated in parallel.

Translation stages: In some instances, the disclosed systems may comprise a translation stage configured to position surfaces or containers, e.g., culture plate wells or other culture containers, relative to the optical axis and/or focal plane of the microscope or imaging system used to acquire images, and to position selected cells relative to the focal point of a laser beam delivered by means of the microscope or imaging system objective. In some instances, the system may comprise a scanning mechanism, e.g. a series of programmable mirrors or a micromirror array, configured to deliver laser light to the position coordinates of one or more cells selected for ablation.

In some instances, the disclosed methods and systems may utilize a high precision X-Y (or in some cases, an X-Y-Z) translation stage for re-positioning the surface or container, e.g., culture plate well or other culture container (in any of the formats described below) in relation to the optical axis and/or focal plane of the microscope or imaging module. Suitable translation stages are commercially available from a number of vendors, for example, Parker Hannifin. Precision translation stage systems can comprise a combination of several components including, but not limited to, linear actuators, optical encoders, servo and/or stepper motors, and motor controllers or drive units. In some cases, high precision and repeatability of stage movement can be required for the systems and methods disclosed herein in order to ensure accurate positioning of individual cells targeted for ablation. Consequently, the methods and systems disclosed herein may further comprise specifying the precision and/or repeatability with which the translation stage is capable of positioning a cell in relation to the optical axis of the microscope or imaging module, or in relation to the focal spot of the laser light beam. In some instances, the precision and/or repeatability of the translation stage may range from about 0.5 μm to about 5 μm. In some instances, the precision and/or repeatability of the translation stage may be at least 0.5 μm, at least 1 μm, at least 2 μm, at least 3 μm, at least 4 μm, or at least 5 μm. In some instances, the precision and/or repeatability of the translation stage may be at most 5 μm, at most 4 μm, at most 3 μm, at most 2 μm, at most 1 um, or at most 0.5 μm. Any of the lower and upper values described in this paragraph may be combined to form a range included within the present disclosure, for example, in some instances the precision and/or repeatability of the translation stage may range from about 1 µm to about 4 µm. Those of skill in the art will recognize that the precision and/or repeatability of the translation stage may have any value within this range, e.g., 1.25 µm.

Containers, e.g., culture plates and other culture containers: Any of a variety of containers, e.g., culture plates or other culture containers may be used when implementing the disclosed methods and systems. Examples include, but are not limited to, Nunc™ 6-well, 12-well, 24-well, 48-well, 96-well, 384-well, and 1536-well culture plates (ThermoFisher Scientific, Waltham, Mass.), Corning® biologically-coated culture flasks and plates (Corning, Inc. Corning, N.Y.), and the CELLSTAR® series of culture flasks, dishes, and multiwell plates from Greiner Bio-One (Greiner Bio-One North America, Inc., Monroe, N.C.).

In some instances, one or more surfaces within the containers, e.g., culture plate wells or other culture container used with the disclosed methods and systems may comprise a coating designed to improve cell adhesion and/or cell viability. Examples of suitable coatings include, but are not limited to, collagen, fibronectin, gelatin, laminin, poly-L-lysine, poly-D-lysine, vitronectin, and the like, or any combination thereof.

In some instances of the disclosed methods and systems, cells may be on, or grown on, a substrate surface, e.g., the top surface of a glass, fused-silica, or polymer substrate. In some instances, the surface may comprise partitions that divide the substrate surface into one or more discrete regions. In some instances, the discrete regions within which cells are cultured may be configured as one-dimensional or two-dimensional arrays, and may be separated from one another by means of, e.g., a patterned hydrophobic coating or thin metal layer. In other aspects, the discrete regions may comprise indents in the substrate surface. In still other aspects, the discrete regions may be separated from each other by means of a well-forming component such that the substrate forms the bottom of a microwell plate (or microplate), and each individual discrete region forms the bottom of one well in the microwell plate. In one aspect of the present disclosure, the well-forming component separates the top surface of the substrate into 96 separate wells. In another aspect, the well-forming component separates the top surface of the substrate into 384 wells. In yet another aspect, the well-forming component separates the top surface of the substrate into 1,536 wells. In all of these aspects, the substrate, whether configured in a planar array, indented array, or microwell plate format, may comprise a disposable or consumable device or cartridge that interfaces with other optical and mechanical components of the disclosed systems.

The methods and systems disclosed herein may further comprise specifying the number of discrete regions or wells into which the substrate surface is divided, irrespective of how separation is maintained between discrete regions or wells. Having larger numbers of discrete regions or wells on a substrate may be advantageous in terms of increasing the processing throughput of the disclosed methods. In one aspect of the present disclosure, the number of discrete regions or wells per substrate may range from about 10 to about 1,600. In other aspects, the number of discrete regions or wells may be at least 10, at least 20, at least 50, at least 100, at least 200, at least 300, at least 400, at least 500, at least 750, at least 1,000, at least 1,250, at least 1,500, or at least 1,600. In yet other aspects of the disclosed methods and systems, the number of discrete regions or wells may be at most 1,600, at most 1,500, at most 1,000, at most 750, at most 500, at most 400, at most 300, at most 200, at most 100, at most 50, at most 20, or at most 10. In a preferred aspect, the number of discrete regions or wells is 96. In another preferred aspect, the number of discrete regions or wells is 384. In yet another preferred aspect, the number of discrete regions or wells is 1,536. Those of skill in the art will appreciate that the number of discrete regions or wells may fall within any range bounded by any of these values (e.g. from about 12 to about 1,400), and may have any value within this range, e.g., 25 discrete regions or wells.

The methods and systems disclosed herein may also comprise specifying the surface area of the discrete regions or wells into which the substrate surface is divided, irrespective of how separation is maintained between discrete regions or wells. Having discrete regions or wells of larger area may facilitate ease-of-access and manipulation of the cultured cells in some cases, whereas having discrete regions or wells of smaller area may be advantageous in terms of reducing culture medium volume requirements and/or increasing the processing throughput of the disclosed methods. In one aspect of the present disclosure, the surface area of the discrete regions or wells is between 1 $mm^2$ and 100 $mm^2$. In other aspects, the area of the discrete regions or wells is at least 1 $mm^2$, at least 2.5 $mm^2$, at least 5 $mm^2$, at least 10 $mm^2$, at least 20 $mm^2$, at least 30 $mm^2$, at least 40 $mm^2$, at least 50 $mm^2$, at least 75 $mm^2$, or at least 100 $mm^2$. In yet other aspects of the disclosed methods and systems, the area of the discrete regions or wells is at most 100 $mm^2$, at most 75 $mm^2$, at most 50 $mm^2$, at most 40 $mm^2$, at most 30 $mm^2$, at most 20 $mm^2$, at most 10 $mm^2$, at most 5 $mm^2$, at most 2.5 $mm^2$, or at most 1 $mm^2$. In a preferred aspect, the area of discrete regions or wells is about 35 $mm^2$. In another preferred aspect, the area of the discrete regions or wells is about 8.6 $mm^2$. Those of skill in the art will appreciate that the area of the discrete regions or wells may fall within any range bounded by any of these values (e.g. from about 2 $mm^2$ to about 95 $mm^2$) and may have any value within this range, e.g., 64 $mm^2$.

Environmental control chamber or module: In some instances, the systems of the present disclosure may comprise an environmental control chamber or module for maintaining the cells to be imaged and selected for retention or destruction at a specified temperature, humidity, $O_2$ concentration, $CO_2$ concentration, $N_2$ concentration, etc., or any combination thereof. In some instances, the environmental chamber may encompass all or a portion of the remaining system components. In some instances, the environmental chamber may be configured to make contact with or encompass only the cell culture containers being processed, e.g., it maybe sized and adapted to be mounted on the translation stage.

Examples of environmental control chambers that may be suitable for implementation of the disclosed methods and systems include, but are not limited to, the enclosures available from Okolab (San Bruno, Calif.), Olympus (Center Valley, Pa.), Zeiss (Thornwood, N.Y.), and others.

Fluid-handling robotics: As noted above, in some instances the systems disclosed herein may further comprise an automated, programmable fluid-dispensing (or liquid-dispensing) system for use in depositing cells from a dilute suspension into culture plate wells or other culture containers. Suitable automated, programmable fluid-dispensing systems are commercially available from a number of vendors, e.g., Beckman Coulter Life Sciences (Indianapolis, Ind.), Perkin Elmer (Waltham, Mass.), Tecan (Baldwin Park, Calif.), Agilent-Velocity 11 (Menlo Park, Calif.), and many others. In some aspects of the disclosed methods and systems, the fluid-dispensing system may comprise a multi-channel dispense head, e.g. a 4 channel, 8 channel, 16 channel, 96 channel, or 384 channel dispense head, for simultaneous delivery of programmable volumes of a cell suspension, culture medium, or other liquid (e.g., volumes ranging from about 1 microliter to several milliliters) to multiple culture plate wells, locations on a substrate surface, etc.

Plate handling robotics: In some instances, the systems disclosed herein may further comprise a culture plate-handling (or culture container-handling) robotic system for automated replacement and positioning of culture plates or containers (in any of the formats described above) in relation to the fluid-dispensing system and/or in relation to the translation stage and/or optical axis of the microscope or imaging module. Suitable automated, programmable plate-handling robotic systems are commercially available from a number of vendors, including Beckman Coulter Life Sciences (Indianapolis, Ind.), Perkin Elmer (Waltham, Mass.), Tecan (Baldwin Park Calif.), Agilent-Velocity 11 (Menlo Park, Calif.), and many others. In some aspects of the methods and systems disclosed herein, the automated plate-handling robotic system may be configured to move containers, e.g., culture plates or culture containers back and forth between the disclosed laser ablation systems and longer-term cell culture incubators.

Processors, controllers, or computers: In some instances, the disclosed systems may comprise one or more processors, controllers, or computers that are configured to execute programmable, software-encoded instructions for: (i) setting and maintaining the environmental parameters within an environmental control chamber (e.g., temperature, humidity, $O_2$ concentration, $CO_2$ concentration, etc.) to optimize and/or maintain cell viability during imaging, (ii) controlling illumination light settings (e.g., intensity and wavelength) and image acquisition (e.g., exposure time, exposure frequency, number of images acquired, etc.), (iii) controlling image pre-processing (e.g., correction of image contrast and brightness, correction for non-uniform illumination, correction for an optical aberration, removal of noise, etc., or any combination thereof) and/or image processing (identification of objects (e.g., cells or sub-cellular structures) within each of the images in a series of one or more images, segmentation of each image to isolate the identified objects, tiling of segmented images to create composite images, performing feature extraction (e.g., identification and/or quantitation of object properties such as observable cellular phenotypic traits), determining the position coordinates for one or more selected cells, determining a confidence level for the destruction of the selected cells from one or more images acquired after performing the ablation step etc., or any combination thereof), (iv) controlling the laser targeting system for ablating unwanted cells (e.g., reading the position coordinates of the selected cells and re-positioning the translation stage such that the selected cells are sequentially positioned within the focal spot of the laser beam; controlling the intensity and/or duration of the laser light to which the selected cells are exposed), or any combination of these steps.

In some instances, the one or more processors, controllers, or computers of the disclosed systems may be further configured to execute programmable, software-encoded instruction for controlling the deposition of cells from a dilute cell suspension into containers, e.g., culture plate wells or other culture containers, using a robotic fluid-dispensing system.

In some instances, the one or more processors, controllers, or computers of the disclosed systems may be further configured to execute programmable, software-encoded instruction for controlling a plate-handling robotic system that moves surfaces or containers, e.g., culture plates or other culture containers, back and forth between the laser ablation system and long-term cell culture incubators.

In some instances, the one or more processors, controllers, or computers of the disclosed systems may comprise a network interface (and associated software) for transferring surface or container, e.g., culture plate tracking data, image data, cell identification and ablation data, and/or other experimental data from the laser ablation system to a laboratory information management system (LIMS).

In some instances, the one or more processors of the disclosed systems may comprise a hardware processor such as a central processing unit (CPU), a graphic processing unit (GPU), a general-purpose processing unit, or computing platform. The one or more processors may be comprised of any of a variety of suitable integrated circuits (e.g., application specific integrated circuits (ASICs) designed specifically for implementing the disclosed image processing-based methods, or field-programmable gate arrays (FPGAs) to accelerate compute time, etc., and/or to facilitate deployment), microprocessors, emerging next-generation microprocessor designs (e.g., memristor-based processors), logic devices and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

The one or more processors or computers used to implement the disclosed methods may be part of a larger computer system and/or may be operatively coupled to a computer network (or a "network") with the aid of a communication interface to facilitate transmission of and sharing of data and surface or container, e.g., culture plate processing results. The network may be a local area network, an intranet and/or extranet, an intranet and/or extranet that is in communication with the Internet, or the Internet. The network in some cases is a telecommunication and/or data network. The network may include one or more computer servers, which in some cases enables distributed computing, such as cloud computing. The network, in some cases with the aid of the computer system, may implement a peer-to-peer network, which may enable devices coupled to the computer system to behave as a client or a server.

The computer system may also include memory or memory locations (e.g., random-access memory, read-only memory, flash memory, Intel® Optane™ technology), electronic storage units (e.g., hard disks), communication interfaces (e.g., network adapters) for communicating with one or more other systems, and peripheral devices, such as cache, other memory, data storage and/or electronic display adapters. The memory, storage units, interfaces and peripheral devices may be in communication with the one or more processors, e.g., a CPU, through a communication bus, e.g., as is found on a motherboard. The storage unit(s) may be data storage unit(s) (or data repositories) for storing data.

The one or more processors, e.g., a CPU, execute a sequence of machine-readable instructions, which are embodied in a program (or "software"). The instructions are stored in a memory location. The instructions are directed to the CPU, which subsequently program or otherwise configure the CPU to implement the methods of the present disclosure. Examples of operations performed by the CPU include fetch, decode, execute, and write back. The CPU may be part of a circuit, such as an integrated circuit. One or more other components of the system may be included in the circuit. In some cases, the circuit is an application specific integrated circuit (ASIC).

In some instances, a computer system of the present disclosure may comprise a storage unit that stores files, such as drivers, libraries and saved programs. The storage unit may store user data, e.g., user-specified preferences and user-specified programs. The computer system in some cases may include one or more additional data storage units that are external to the computer system, such as located on a remote server that is in communication with the computer system through an intranet or the Internet.

Software: Some aspects of the methods and systems provided herein, such as the disclosed methods for selecting and ablating cells in a culture plate well, are implemented by way of machine-executable code (processor-executable code) stored in an electronic storage location of the computer system, such as, for example, in the memory or electronic storage unit. The machine-executable or machine-readable code is provided in the form of software. During use, the code is executed by the one or more processors. In some cases, the code is retrieved from the storage unit and stored in the memory for ready access by the one or more processors. In some situations, the electronic storage unit is precluded, and machine-executable instructions are stored in memory. The code may be pre-compiled and configured for use with a machine having one or more processors adapted to execute the code or may be compiled at run time. The code may be supplied in a programming language that is selected to enable the code to execute in a pre-compiled or as-compiled fashion.

Various aspects of the disclosed method and systems may be thought of as "products" or "articles of manufacture", e.g., "computer program or software products", typically in the form of machine (or processor) executable code and/or associated data that is stored in a type of machine readable medium, where the executable code comprises a plurality of instructions for controlling a computer or computer system in performing one or more of the methods disclosed herein. Machine-executable code may be stored in an optical storage unit comprising an optically readable medium such as an optical disc, CD-ROM, DVD, or Blu-Ray disc. Machine-executable code may be stored in an electronic storage unit, such as memory (e.g., read-only memory, random-access memory, flash memory) or on a hard disk. "Storage" type media include any or all of the tangible memory of the computers, processors or the like, or associated modules thereof, such as various semiconductor memory chips, optical drives, tape drives, disk drives and the like, which may provide non-transitory storage at any time for the software that encodes the methods and algorithms disclosed herein.

All or a portion of the software code may at times be communicated via the Internet or various other telecommunication networks. Such communications, for example, enable loading of the software from one computer or processor into another, for example, from a management server or host computer into the computer platform of an application server. Thus, other types of media that are used to convey the software encoded instructions include optical, electrical and electromagnetic waves, such as those used across physical interfaces between local devices, through wired and optical landline networks, and over various atmospheric links. The physical elements that carry such waves, such as wired or wireless links, optical links, or the like, are also considered media that convey the software encoded instructions for performing the methods disclosed herein. As used herein, unless restricted to non-transitory, tangible "storage" media, terms such as computer or machine "readable medium" refer to any medium that participates in providing instructions to a processor for execution.

The computer system typically includes, or may be in communication with, an electronic display for providing, for example, images captured by a machine vision system. The display is typically also capable of providing a user interface (UI). Examples of UI's include but are not limited to graphical user interfaces (GUIs), web-based user interfaces, and the like.

Figure 3:
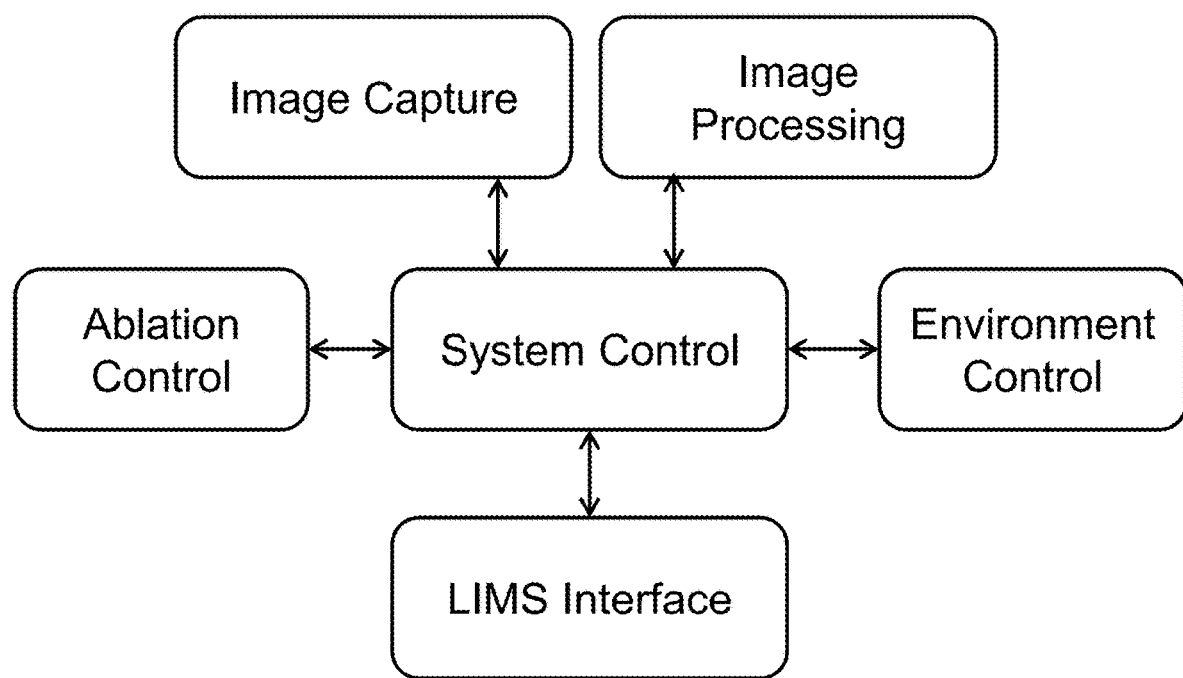
FIG. 3 provides a block diagram for the software used to control a system for laser photoablation of cells in a cell culture according to one aspect of the present disclosure.

FIG. 3 provides a block diagram for system control software used to control a laser photoablation system according to one aspect of the present disclosure. In some instances, the control software may comprise machine-readable or machine-executable instructions for communicating with and/or controlling: (i) an image acquisition module, (ii) an image processing module, (iii) an ablation control module (e.g., a cell targeting and laser exposure control module), (iv) an environment control module, and/or (v) a LIMS interface, or any combination of these steps. In some instances the system control software may further comprise software for interfacing the laser ablation systems of the present disclosure with: (vi) a fluid-handling system used to dispense cells onto a surface or into a container, e.g., culture plate wells or other culture containers, and/or (vii) a robotic plate-handling system for moving surfaces or containers, e.g., culture plates or other culture containers, back and forth between the fluid-handling system, the laser ablation system, and/or a long-term cell culture incubator.

In some instances, the system control software and all component modules thereof may be executed by a single processor or computer. In some instances, the system control software and one or more of the component modules may be performed on different processors or computers. In some instances, all or a portion of the system control software and/or component modules thereof may be performed by a computer network and/or cloud-based computing system.

System performance specifications: In general, the systems disclosed herein will be configured to perform the disclosed methods for cell identification, selection, and ablation with performance specifications for photoablation rate, percentage of cells ablated, efficiency for rendering ablated cells as non-viable, processing throughput, and percentage of processed surfaces or containers, e.g., culture plate wells or culture containers, containing a single viable cell following the photoablation step as described under the methods section above.

Applications: The methods and systems disclosed herein are generally applicable to the preparation of clonal populations of cells. Examples of specific applications to which the disclosed methods and systems may be applied include, but are not limited to, destruction of undifferentiated stem cells in an in vitro differentiated stem cell culture, destruction of differentiated stem cells in an in vitro undifferentiated stem cell culture, isolation of single stem cells and preparation of clonal stem cell colonies, isolation of single cells (e.g., cells expressing a successful CRISPR editing parameter) and preparation of clonal cell colonies therefrom, preparation of clonal populations of plant cells, and the like.

EXAMPLES

These examples are provided for illustrative purposes only and not to limit the scope of the claims provided herein.

Example 1—Prototype Laser Ablation System

A prototype imaging-based cell targeting and laser ablation system was constructed that comprised: (i) a microscope (Zeiss (Jena, Germany) Axio Observer 7) for viewing cells in culture dishes and plates, (ii) a Zeiss microscope focusing system for keeping cells in focus, (iii) a laser (Hamilton Thorne (Beverly, Mass.) Stiletto laser) and objective (Hamilton Thorne (Beverly, Mass.) 20× Objective) that are capable of working in tandem to focus light on a specific location in the culture container, (iv) a camera system (Lumenera (Ottawa, Canada) Infinity3 camera) used to record the location, presence, and absence of cells in the culture container, (v) custom software that performed image capture and ablation control (which may optionally be updated for integration with a software control structure that tracks the process (to keep track of the clonal production if the ablation system is part of a larger workflow), and (vi) a custom environmental control system that kept the container holding the cells to be ablated under a specified set of culturing conditions (5% $CO_2$ and 37 C; the gas mixture was bubbled through water to provide constant humidity).

Figure 4:
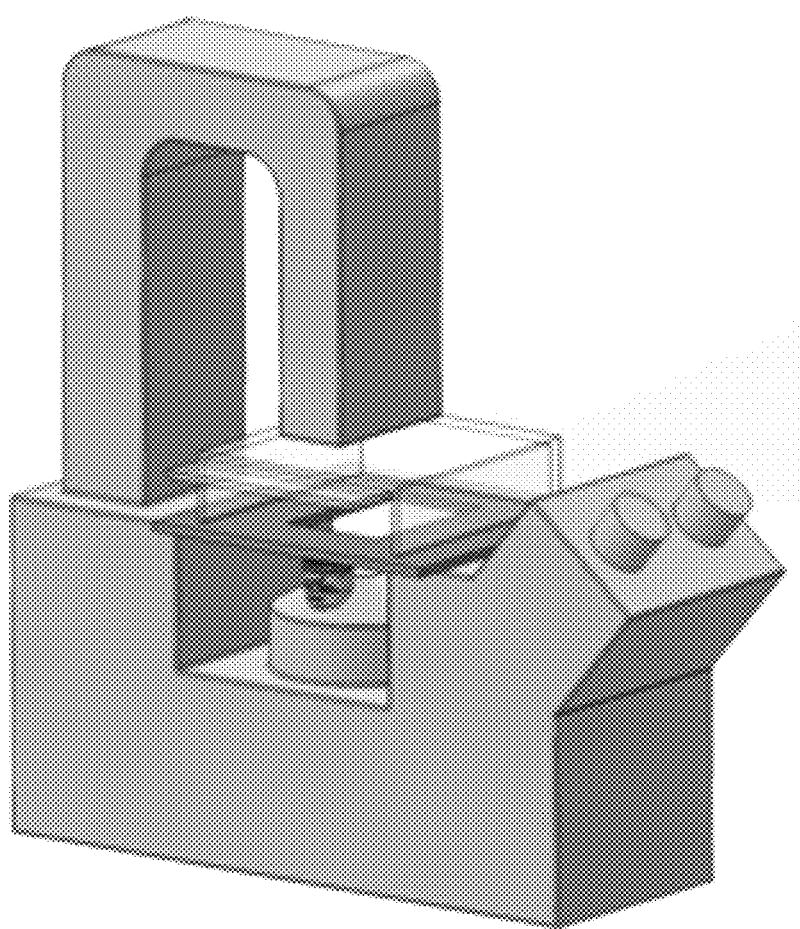
FIG. 4 provides a CAD model (isometric view) of an inverted microscope used to perform laser photoablation of cells in a cell culture according to one aspect of the present disclosure.
Figure 5:
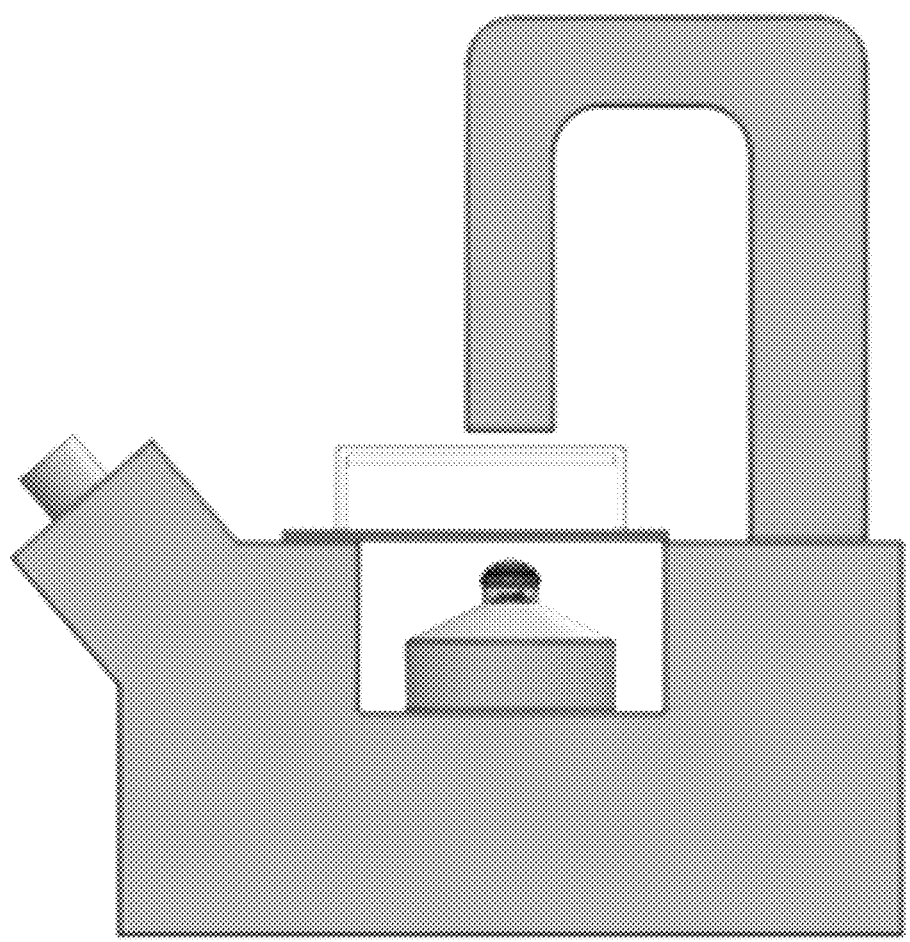
FIG. 5 provides a CAD model (side view) of an inverted microscope used to perform laser photoablation of cells in a cell culture according to one aspect of the present disclosure.

FIG. 4 provides a CAD model (isometric view) and FIG. 5 provides a CAD model (side view) of the inverted microscope used to assemble the prototype laser ablation system. As can be seen in the model views, a culture flask was positioned on the microscope stage and viewed from below using the inverted microscope optics. A light beam from a laser (not shown) was directed into the rear of the microscope base and delivered to the sample plane via the overhead optical path.

Figure 6:
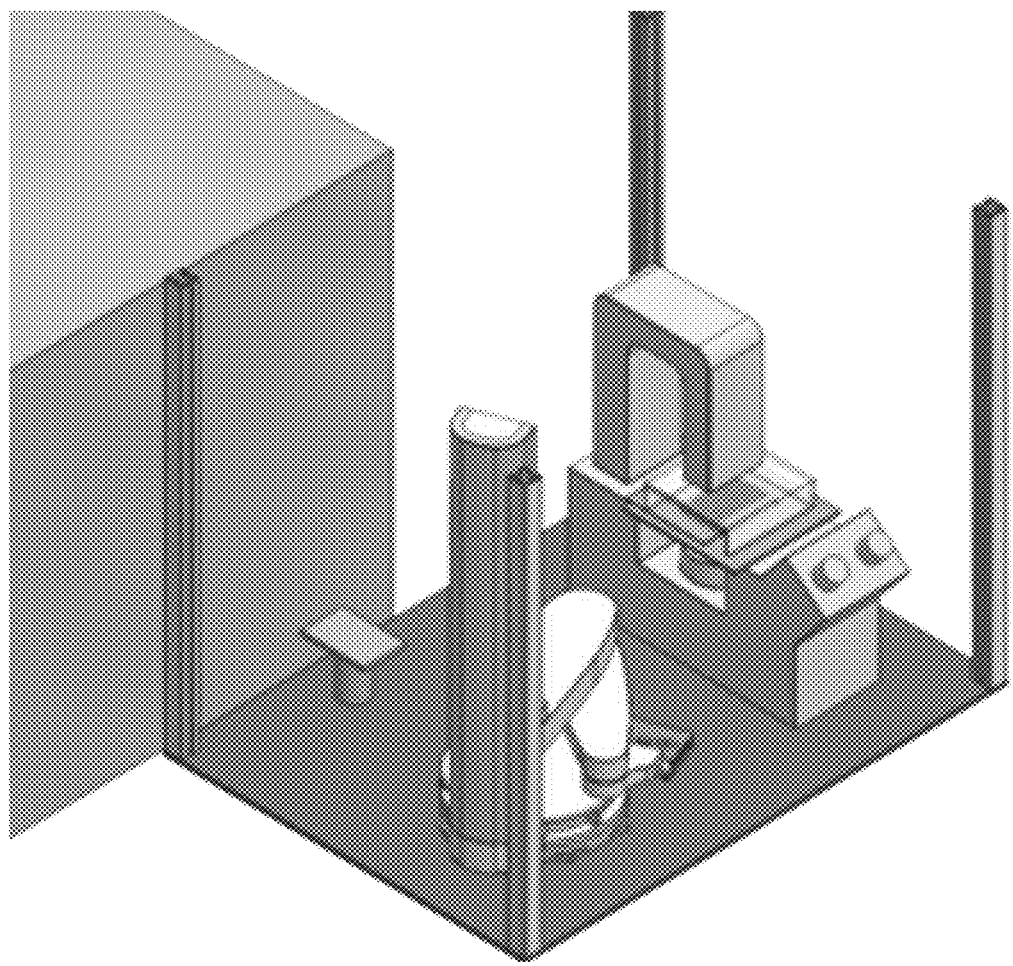
FIG. 6 provides a CAD model of the microscope of FIGS. 4 and 5 along with optical elements used to couple laser light into the microscope, and a housing (removed in this view) used to control the imaging environment.

FIG. 6 provides a CAD model of the microscope of FIGS. 4 and 5 along with optical elements used to couple laser light from a diode laser operating at approximately 1,440-1,450 nm at a pulse rate of approximately 16 pulses per millisecond into the microscope, and a housing (removed in this view) used to control the imaging environment.

HEK293 and HT1080 cells were plated in culture plates and grown in a complete serum-free, low-protein 293 SFMII growth medium (Thermo-Fisher Scientific, Waltham, Mass.) supplemented with 4 mM L-glutamine at 37 C and 5% $CO_2$. Custom software was used to program the targeting coordinates of cells for ablation. The culture plates were monitored over the course of several days to ensure that the retained cells survived.

Figure 7A:
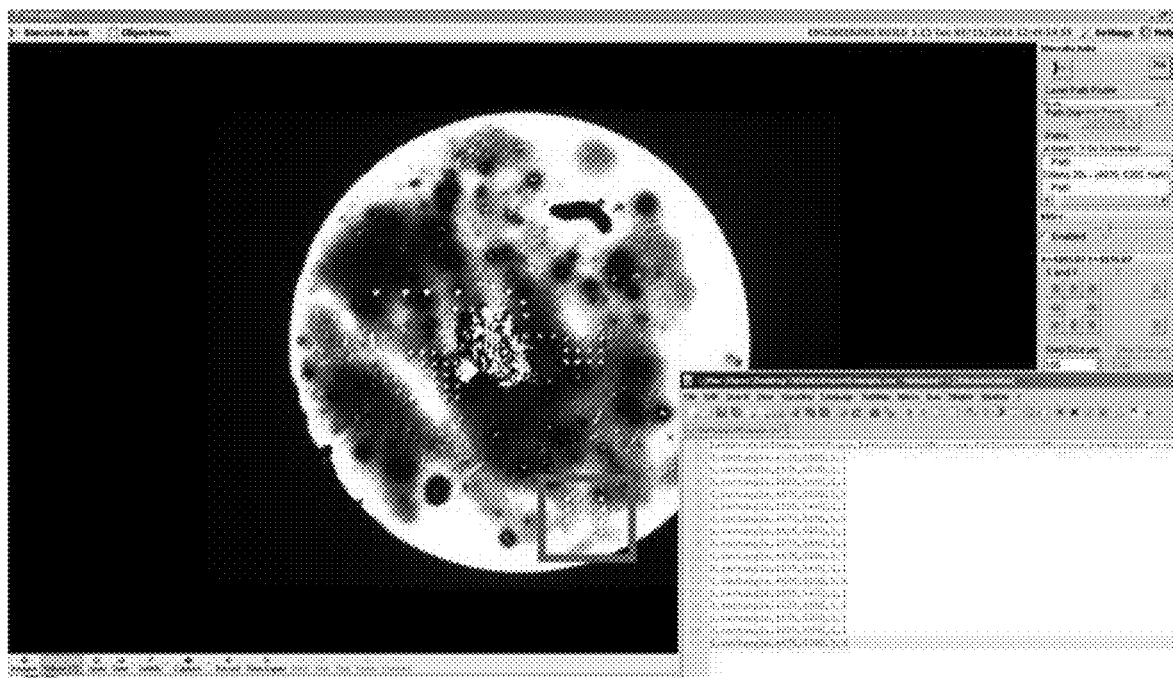
FIGS. 7A-B show non-limiting examples of data that illustrate the use of laser photoablation to remove cells and create patterns in a confluent cell culture.
Figure 7B:
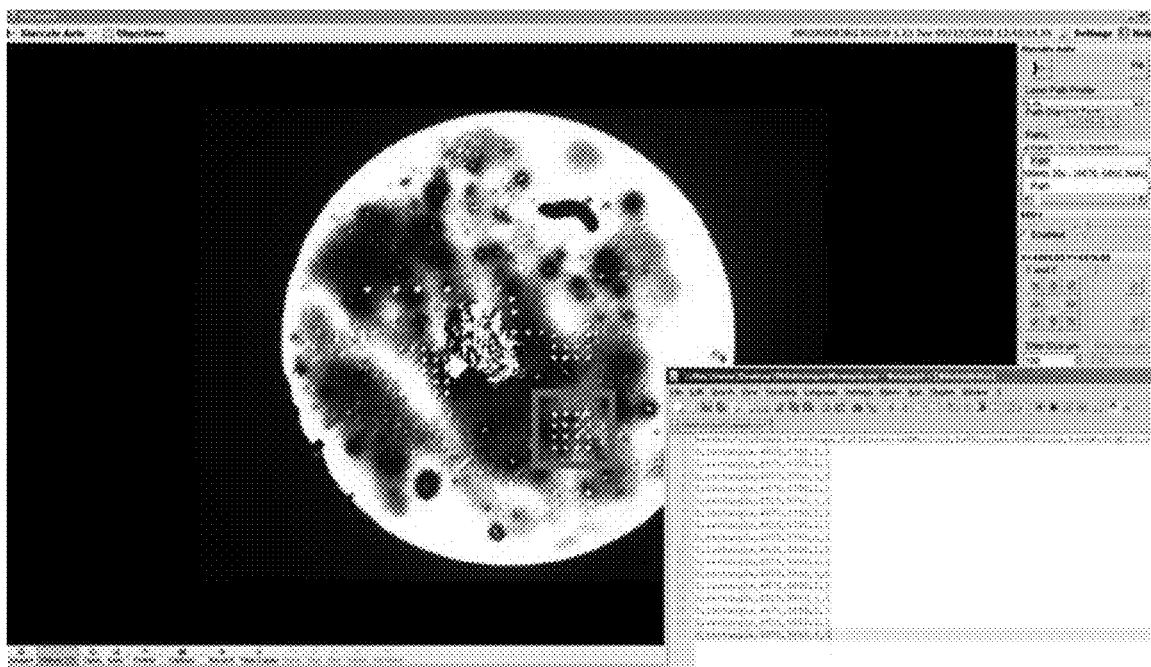

FIGS. 7A-B show non-limiting examples of data that illustrate the use of the prototype laser ablation system to remove HEK293 cells and create patterns in a confluent cell culture. FIG. 7A: a pattern of cells was destroyed by laser photoablation according to a specified set of position coordinates (box). FIG. 7B: a subsequent photoablation pattern performed on the same cell culture according to an updated set of position coordinates (box).

Figure 8A:
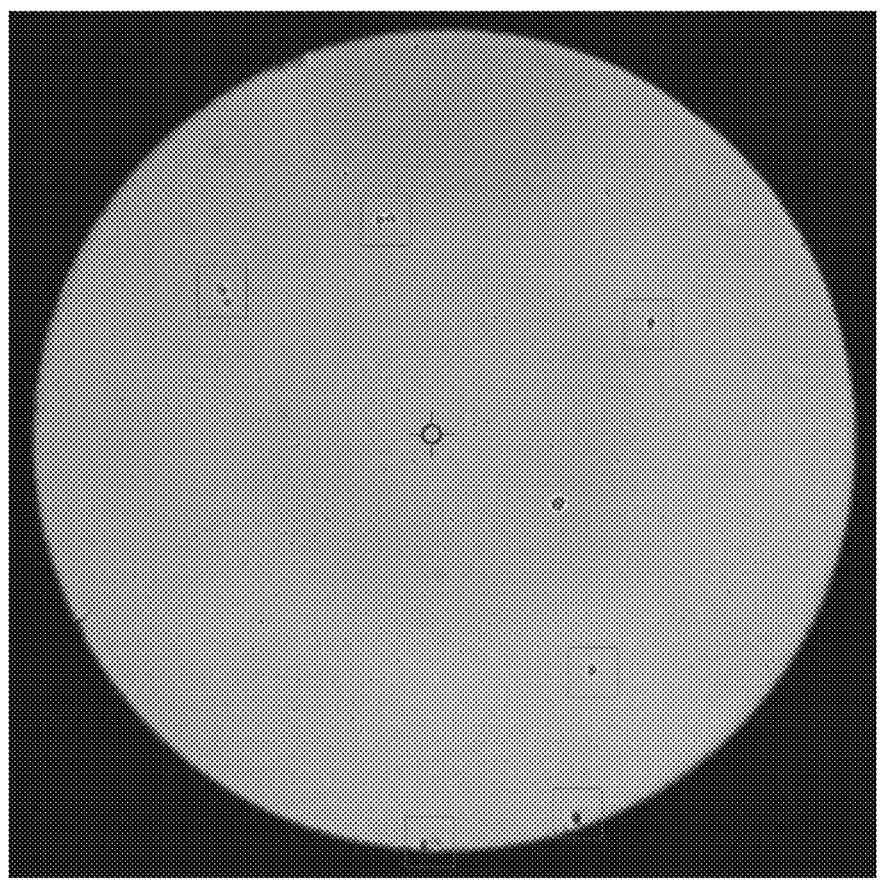
FIGS. 8A-B show non-limiting examples of image data that illustrate the use of laser photoablation to destroy single cells.
Figure 8B:
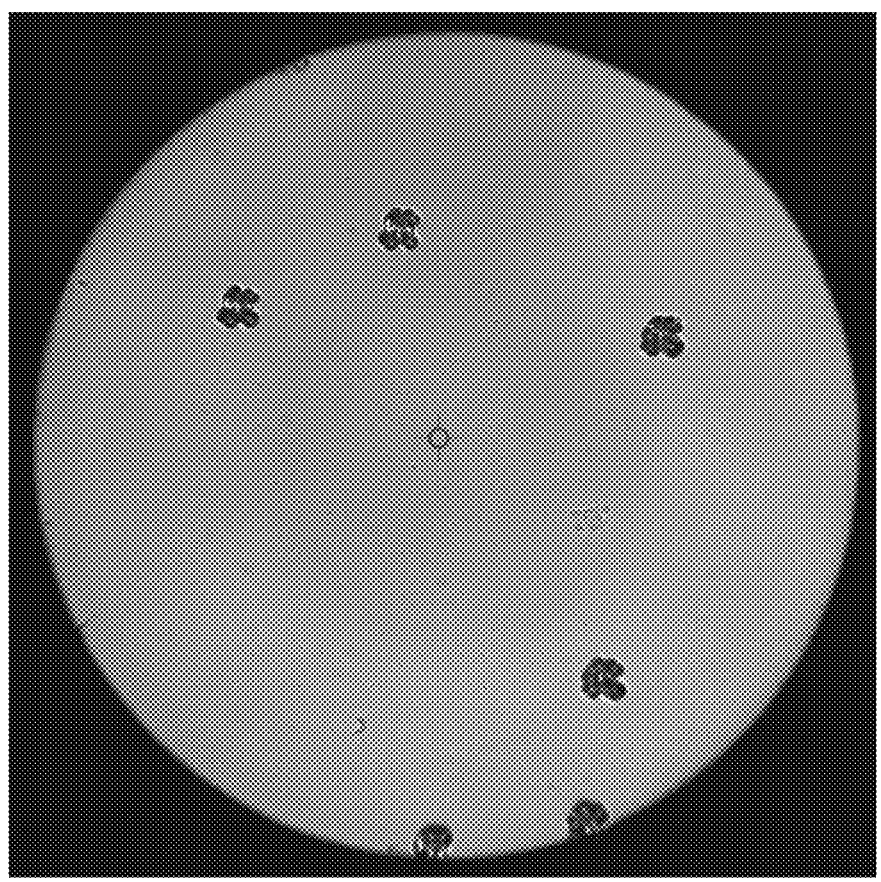

FIGS. 8A-B show non-limiting examples of bright-field image data that illustrate the use of a prototype laser ablation system to destroy single HEK293 cells. FIG. 8A: image of a cell culture plate showing three targeted single cells as indicated in the boxes. FIG. 8B: image of the same cell culture plate following the destruction of the targeted cells by laser photoablation.

Example 2—Laser Power Study

The software for a commercially-available Hamilton Thorne Stiletto® (Hamilton Thorne, Beverly, Mass.) laser system allows the user to control laser power (% of maximum; 300 mW peak power), laser pulse length (100-3000 µs), and pulse frequency (1-200 Hz). We have modified the software that integrates and controls the components of the laser system, e.g., a laser, translation stage, and camera, to enable independent application development. In this example, we have modified the system integration software to enable operation in a continuous mode where laser power (%) can be changed, and to enable operation in single laser pulse mode where both laser power (%) and pulse length (µs) can be controlled. A study was designed to determine optimal laser power levels for ablating cells from a given area using a continuous raster pattern without killing neighboring cells, as well as to determine the optimal power and pulse length requirements for killing individual cells using single laser pulses. These measurements were made in confluent sheets of HEK293 cells, and cell death was determined by propidium iodide (PI) fluorescence, a marker of cell membrane integrity where dead cells fluoresce red. For raster mode measurements, a 10 µm×10 µm square was ablated at 10%-100% laser power with 24 replicates per condition. For single pulse mode, a point was ablated using 100-300 µs pulse lengths and 10-100% laser power with 3 replicates per condition.

Figure 9:
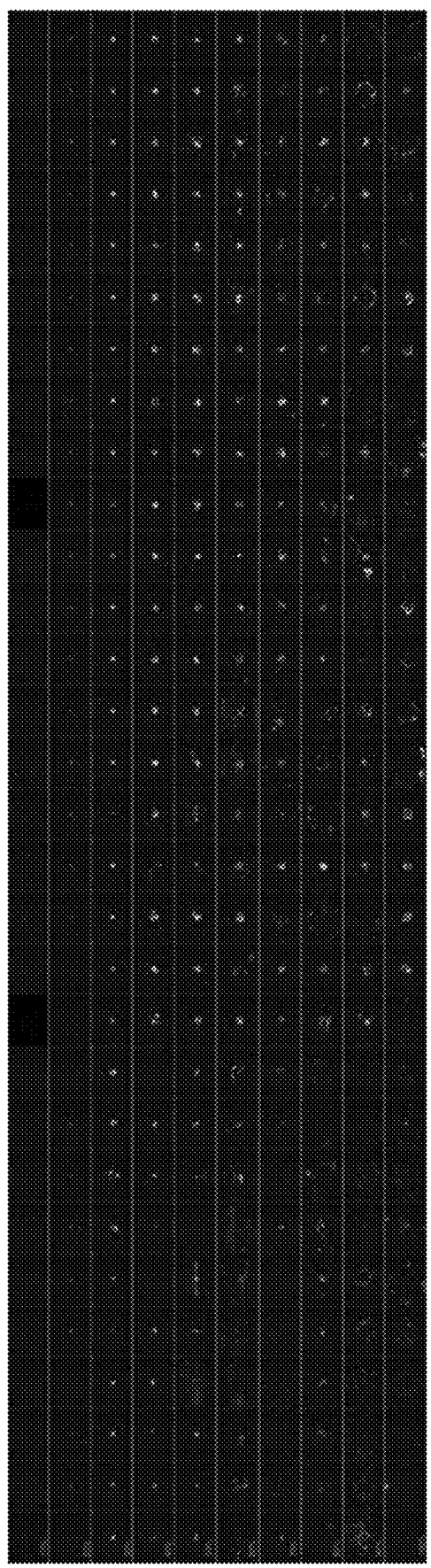
FIG. 9 provides a non-limiting example of laser photoablation data where cells were selectively ablated using a raster pattern of exposure to continuous laser light.

FIG. 9 provides a non-limiting example of laser photoablation data where cells were selectively ablated using a continuous raster pattern of exposure to laser light. Using 20% laser power was sufficient to kill cells in a small area. Increasing laser power expands the killing area, while using 60% laser power or higher resulted in detachment of cells.

Figure 10:
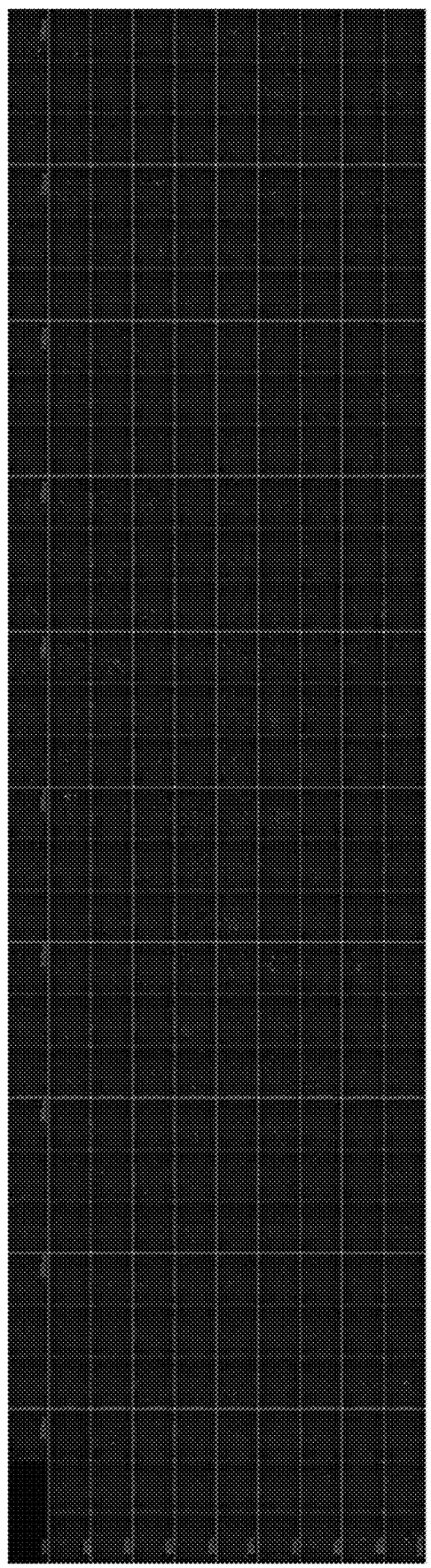
FIG. 10 provides a non-limiting example of laser photoablation data where cells were selectively ablated using exposure to single pulses of laser light.

FIG. 10 provides a non-limiting example of laser photoablation data where cells were selectively ablated using exposure to single pulses of laser light. Single pulse point ablation did not produce an unambiguous pattern of cell killing. Use of 100% laser power resulted in the killing of clusters of cells at several longer pulse lengths (300 µs, 280 µs, 260 µs), but there was considerable variability in the percentage of cells killed.

These results demonstrate that the use of continuous rastering of laser light at a laser power lower than 20% was insufficient to kill cells, while the use of laser power levels of greater than 40% led to increasingly large areas of cell death for a 10 µm×10 µm raster area. The efficacy of single pulse laser irradiation proved to be highly variable in this study, with long (260+ µs), high power (70%+) pulses capable of killing multiple cells per area. However, the data for single pulse irradiation appears to be considerably noisier than that for area ablation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:

1. A method comprising:
a) selecting a cell based on its position on one or more surfaces or in one or more containers, wherein the selecting is not based on whether the cell comprises an exogenous label or an expressed reporter and wherein the selecting is performed using an imaging technique and an automated image analysis process; and
b) photoablating at least 80% of five or more cells on each of the one or more surfaces or in each of the one or more containers, wherein at least 95% of the one or more surfaces or containers contain only one viable cell after the photoablating is performed, wherein the cell selected in (a) is not photoablated.

2. The method of claim 1, wherein b) comprises photoablating all but a first cell of the five or more cells on each of the one or more surfaces or in each of the one or more containers, wherein the first cell is the cell selected in (a).

3. The method of claim 2, further comprising growing a clonal population of the first cell after the photoablating is performed, thereby generating a clonal population of cells.

4. The method of claim 3, further comprising performing an assay on the clonal population of cells.

5. The method of claim 3, further comprising photodetaching one or more cells of the clonal population of cells from the one or more surfaces or one or more containers thereby obtaining one or more photodetached cells.

6. The method of claim 5, further comprising performing an assay on the one or more photodetached cells.

7. The method of claim 5, further comprising growing the one or more photodetached cells.

8. The method of claim 2, wherein the five or more cells comprise about 10 to about 15 cells.

9. The method of claim 2, wherein the photoablating occurs at a rate of at least 60 cells per minute.

10. The method of claim 2, wherein the photoablating occurs with an efficiency of greater than 99%.

11. The method of claim 2, wherein the photoablating occurs using light in the wavelength range of 1440 nm to 1450 nm.

12. The method of claim 1, wherein the selecting is based on a proximity of the first cell to a center of the one or more surfaces or containers, a size of the first cell, a morphology of the first cell, a phenotype of the first cell, a development stage of the first cell, or any combination thereof.

13. The method of claim 1, wherein at least 98% of the one or more surfaces or containers contain only one viable cell after the photoablating is performed.

14. The method of claim 1, wherein the one or more surfaces or containers comprise at least 5, 10, 20, 30, 40, 50, 60, 70, 80, 90, or 100 surfaces or containers.

15. The method of claim 1, wherein the imaging technique comprises bright-field imaging, dark-field imaging, phase contrast imaging or any combination thereof.

16. The method of claim 1, wherein the selecting is based on a proximity of the cell to a center of the one or more surfaces or containers.

17. The method of claim 1, wherein the selecting is based on a size of the cell.

18. The method of claim 1, wherein the selecting is based on a morphology of the cell.

19. The method of claim 1, wherein the selecting is based on a phenotype of the cell.

20. The method of claim 1, wherein the selecting is based on a development stage of the cell.

* * * * *